(12) United States Patent
Kitaoka

(10) Patent No.: US 8,747,745 B2
(45) Date of Patent: Jun. 10, 2014

(54) APPARATUS AND METHOD FOR BIOCHEMICAL ANALYSIS

(75) Inventor: Atsushi Kitaoka, Kisarazu (JP)

(73) Assignee: Canon Kabushiki Kaisha, Tokyo (JP)

( * ) Notice: Subject to any disclaimer, the term of this patent is extended or adjusted under 35 U.S.C. 154(b) by 773 days.

(21) Appl. No.: 12/099,518

(22) Filed: Apr. 8, 2008

(65) Prior Publication Data

US 2008/0254545 A1 Oct. 16, 2008

(30) Foreign Application Priority Data

Apr. 12, 2007 (JP) ................................. 2007-104850

(51) Int. Cl.
- *G01N 21/00* (2006.01)
- *G01N 31/00* (2006.01)
- *G01N 33/00* (2006.01)
- *B01L 3/02* (2006.01)
- *G01N 35/02* (2006.01)
- *G01N 35/00* (2006.01)

(52) U.S. Cl.
USPC .................. 422/65; 422/62; 422/63; 422/509; 422/511; 422/525; 422/526; 436/43; 436/47

(58) Field of Classification Search
USPC ..................... 422/65, 509, 511, 515, 525, 526
See application file for complete search history.

(56) References Cited

U.S. PATENT DOCUMENTS

| | | | |
|---|---|---|---|
| 5,277,871 A | 1/1994 | Fujii et al. | |
| 6,881,315 B2 | 4/2005 | Iida et al. | |
| 2003/0040104 A1* | 2/2003 | Barbera-Guillem | 435/286.2 |
| 2004/0002163 A1* | 1/2004 | Reinhardt et al. | 436/174 |
| 2006/0210435 A1* | 9/2006 | Alavie et al. | 422/65 |
| 2008/0028871 A1 | 2/2008 | Kitaoka | |

FOREIGN PATENT DOCUMENTS

| | | |
|---|---|---|
| JP | 64-084148 A | 3/1989 |
| JP | 3-134560 A | 6/1991 |
| JP | 8-20426 B2 | 3/1996 |
| JP | 11-223635 A | 8/1999 |
| JP | 2002-189033 A | 7/2002 |
| JP | 2004-45357 A | 2/2004 |

* cited by examiner

*Primary Examiner* — Jill Warden
*Assistant Examiner* — Julie Tavares
(74) *Attorney, Agent, or Firm* — Fitzpatrick, Cella, Harper and Scinto

(57) ABSTRACT

An apparatus for analyzing that performs a plurality of treatment operations includes a plurality of treatment units arranged in a vertical direction of the apparatus. The apparatus for analyzing also includes a conveying mechanism configured to convey a sample between the treatment units. The sample is delivered above or in the treatment units. A pipette chip is also delivered above or in the treatment units.

9 Claims, 29 Drawing Sheets

APPARATUS AND METHOD FOR BIOCHEMICAL ANALYSIS

BACKGROUND OF THE INVENTION

1. Field of the Invention

The present invention relates to an apparatus for analyzing, and more particularly, to an apparatus that conducts a biochemical analysis including biochemical reaction treatment for a sample or biochemical detection treatment for a sample, for example, gene detection using a DNA microarray.

2. Description of the Related Art

There has been a strong demand for automation of analysis operations in the technical field of sample analysis.

Gene analysis using a test piece, such as a DNA microarray or a DNA chip, is an example of sample analysis. In a DNA microarray, multiple kinds of nucleic acid probes are fixed as probe spots in a matrix on a surface of a substrate, such as a slide glass or a silicone substrate. The DNA microarray is brought into contact with a sample, such as fluorochrome-labeled DNA, under a hybridization condition. When the DNA microarray and the sample contain nucleic acids that cause a hybridization reaction therebetween, the labeled substance is fixed to the DNA microarray via the nucleic acid probe. By detecting the probe spot to which the labeled substance is bonded, the kind of hybridization-reacted nucleic acid can be identified.

In a typical procedure of gene analysis, (1) an extraction process for extracting nucleic acid from a sample, (2) an amplification process for amplifying the extracted nucleic acid, (3) a process for causing a hybridization reaction between the amplified nucleic acid and a nucleic acid probe in a DNA microarray, and (4) a detection process are performed in that order. Particularly in the processes (1) to (3), it is necessary to perform troublesome operations in handling sample and reagent liquid and handling containers. Therefore, there is a strong demand for automation of the operations from the viewpoints of labor saving and reduction of time.

Besides gene analysis, various analyses are conducted for samples such as body tissue and protein. Automation of these analyses has been demanded similarly.

Some attempts have been proposed to automate sample analyses.

For example, in an automatic apparatus for analyzing disclosed in Japanese Patent Laid-Open No. 11-223635, a device for analyzing a sample in a plate and/or a cleaner for cleaning the plate are disposed below a plate stage having a dispensing member, and a conveying means is provided to convey the plate from the plate stage.

In a liquid chromatographic analyzer and a prelabeling reaction treating method disclosed in Japanese Patent Publication No. 8-20426, a fluorophotometer and a column panel are stacked in the vertical direction. However, this publication does not disclose a specific method of conveyance between the treatment units.

SUMMARY OF THE INVENTION

There has been considered a method in which a user directly transfers a sample between treatment units, and a method in which a sample is transferred, for example, through a liquid feeding pipe connecting the treatment units by a pump or the like. Unfortunately, when the user performs the transfer operation, there is a risk of human error. In contrast, when the liquid feeding pipe is used, contamination of the liquid is inevitable. In any case, it is difficult to overcome the problem of complexity in the operations.

As described above, attempts have been made to automate the sample analysis operation. However, there has not yet been developed any apparatus that copes with the complexity of analysis steps and that also reduces the size of the apparatus, particularly, reduces the footprint.

Accordingly, the present invention provides an apparatus for analyzing that needs a sequence of operations (analysis steps), that can perform complicated operations, and that contributes to size reduction.

An apparatus for analyzing according to an aspect of the present invention includes a plurality of treatment units configured to treat a sample, at least two of the treatment units being arranged in a vertical direction of the apparatus; and a conveying mechanism configured to convey the sample between the treatment units arranged in the vertical direction.

According to the present invention, the footprint of the apparatus for analyzing including a plurality of treatment units can be reduced. Since a sample and a reagent are moved between the treatment units by using the conveying mechanism for conveying the sample, the necessary footprint can be reduced. Pipette chips can be moved between the treatment units with the conveyance of the sample. This can reduce the necessary footprint, and can reduce the number of pipette chips to be used.

Further features of the present invention will become apparent from the following description of exemplary embodiments with reference to the attached drawings.

DESCRIPTION OF THE EMBODIMENTS

Definitions of Terms

Figure 1:
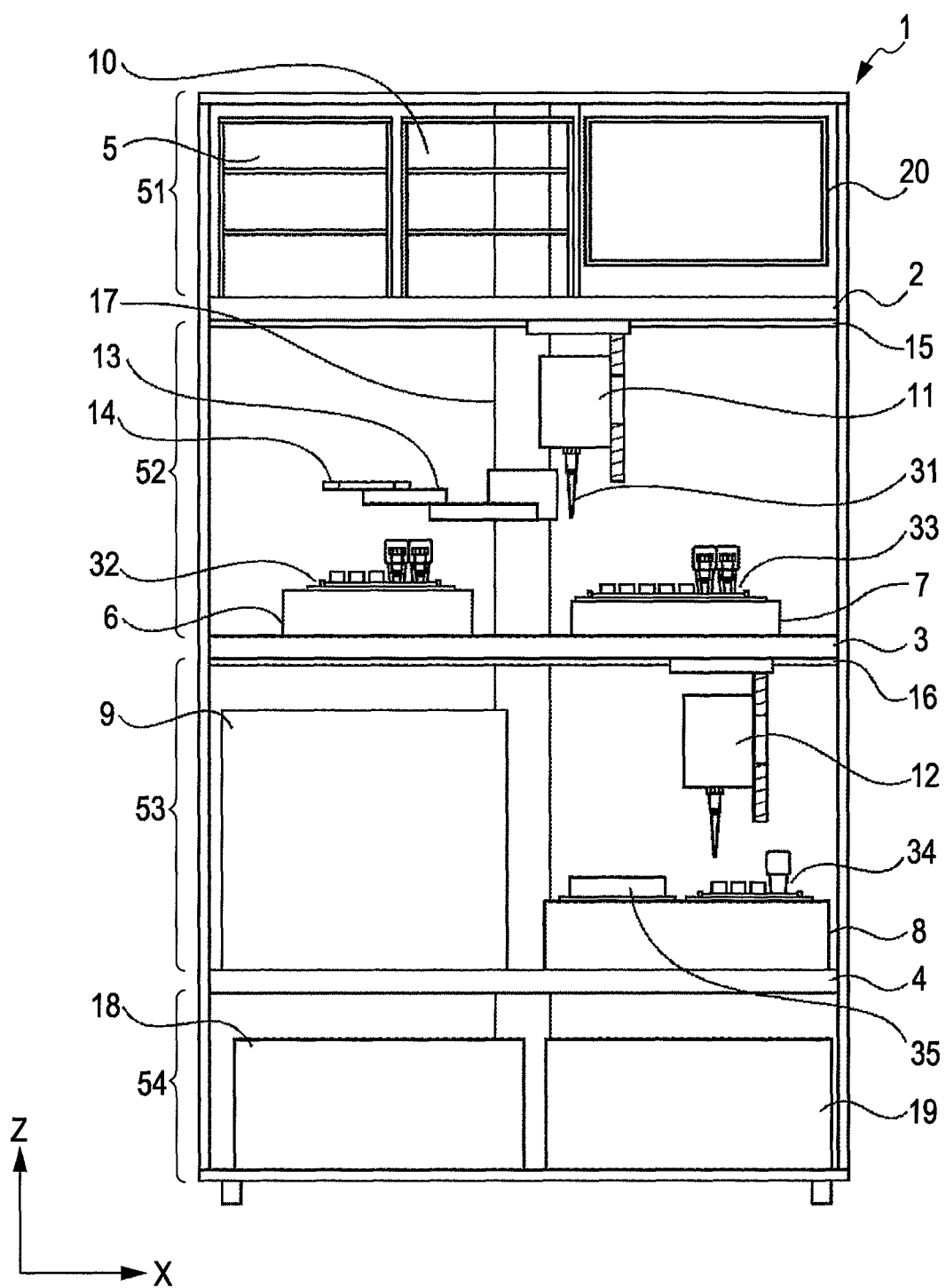
FIG. 1 is a schematic front view of an automatic apparatus for analyzing according to a first exemplary embodiment of the present invention.

Terms used in the description of exemplary embodiments of the present invention will be defined below. Examples given in the description do not limit the scope of the present invention. Unless otherwise specified, the definitions of terms shall be construed to include both plural and singular form of terms.

1. Sample

A sample in the exemplary embodiments of the present invention refers to an object to be analyzed. Examples of samples are substances taken from the living body (e.g., body fluid such as blood, body tissue, feces, urine, and phlegm), substances taken from plants (e.g., a leaf, a stem, a root, a flower, and fruit), substances taken from the environment (e.g., soil, water, dust, and metal), and industrial products (e.g., resin). Sample-derived substances obtained by subjecting the above substances to any treatment are also included in the definition of the sample.

2. Treatment

Treatment in the exemplary embodiments of the present invention refers to an action of aiming to change or observe the characteristic of a substance by exerting an external biotic, chemical, physical, mechanical, or electrical influence on the subject. For example, treatment includes actions of adding a reagent, stirring liquid, adsorbing molecules of nucleic acid to a carrier, controlling the temperature, measuring the temperature, applying an electric field, measuring an electric field, generating vibration, applying pressure, measuring pressure, radiating a light beam, detecting the light quantity, applying a magnetic field, and measuring a magnetic field. Treatment also includes a combination of these actions performed simultaneously or sequentially. Biochemical reaction treatment refers to treatment required to cause a biochemical reaction for analysis, including a process for causing a biochemical reaction, a preprocess performed to cause the biochemical reaction, and a postprocess performed after the biochemical reaction. Biochemical detection treatment refers to treatment for detecting a difference between a state of a sample before the biochemical reaction and a state of the sample after the biochemical reaction. More specifically, biochemical detection treatment includes treatment for detecting fluorescence or chemiluminescence in a reacted hybrid such as a DNA microarray, treatment for measuring the position of a sample after gel electrophoresis, and treatment for detecting a substance that is specifically bonded to a reacted sample in a solution (an intercalator for a hybrid). Samples to be treated in two treatment units may be the same or different.

3. Biochemical Reaction

A biochemical reaction refers to a reaction of a biological substance or tissue (e.g., cell, nucleic acid, protein, virus) caused by a biotic or chemical mechanism. Examples of biochemical reactions are separation of a blood component, spallation of a cell membrane or a cell wall, adsorption of nucleic acid to a carrier, purification of nucleic acid, amplification of nucleic acid, hybridization of nucleic acid, bonding by affinity, and methylation. The biochemical reaction also includes a combination of these reactions.

4. Sample Conveying Mechanism

Sample conveyance refers to moving a sample to a different place. For example, sample conveyance includes actions of discharging a liquid sample from a pipette chip into a container, drawing in a liquid sample from a container by a pipette chip, dropping a solid sample into a container, operating a moving mechanism so as to move a sample held in the mechanism, moving a container holding a liquid sample, and transferring a liquid sample from a chamber to another chamber in a container. A sample conveying mechanism in the exemplary embodiments of the present invention includes, for example, a pipette unit which can hold a pipette chip at a leading end thereof and in which a sample can be drawn into the pipette chip and a sample solution can be discharged from the pipette chip, and a hand robot capable of holding and moving a container having a sample to a predetermined position. It is preferable that these members be combined into a mechanism for conveying a sample between the treatment units.

5. A Plurality of Treatment Units

In the exemplary embodiments of the present invention, a plurality of treatment units is provided to respectively perform the above-described treatment operations. A plurality of treatment units allows different treatment operations to be performed in parallel. As a specific example, an apparatus for analyzing that detects genes with a DNA microarray includes four treatment units, that is, a nucleic-acid extraction unit that extracts nucleic acid from the tissue, a nucleic-acid amplification unit that amplifies the extracted nucleic acid by PCR (polymerase chain reaction) or by other methods, a hybridization unit that reacts the amplified nucleic acid with the DNA microarray, and a detection unit that detects the reaction with the DNA microarray. When two units are provided, for example, the detection unit and the hybridization units are arranged in the vertical direction so that the hybridization unit is provided above the detection unit.

An apparatus for analyzing that uses a chip in which an antigen or an antibody is fixed to a substrate can continuously perform, with two or more treatment units, a reaction process for reacting a sample with the chip, a second reaction process for causing reaction by further adding a secondary antibody to the chip, a cleaning process for removing the antigen or antibody that is not concerned with bonding, and a detection process for measuring the fluorescence intensity of a fluorescent label given to the bonded antigen or antibody.

An apparatus for analyzing using cell culture can continuously perform, with different units, a primary culture process for culturing cells in a culture bottle, a secondary culture process for culturing the cells in a culture medium, and a detection process for optically detecting the number of cultured cells.

6. Vertical Direction

In the exemplary embodiments of the present invention, a vertical direction of an apparatus refers to a vertical direction provided when the apparatus is installed in a state such as to normally operate.

A state in which a plurality of treatment units are arranged in the vertical direction refers to a state in which largest cross sections of the treatment units taken in the horizontal direction overlap with one another, as viewed in the vertical direction.

While the footprint of the apparatus decreases as the overlapping areas between the cross sections increases, the cross sections of all the treatment units do not always need to overlap, and may be designed in accordance with the layout of the treatment units.

It is satisfactory as long as at least two treatment units are arranged in the vertical direction. However, it is preferable that three or four treatment units be arranged in the vertical direction. Alternatively, five or more treatment units may be arranged in the vertical direction.

The number of axes extending in the vertical direction in the apparatus is not limited to one, and may be two or more. That is, it is possible to adopt a two-axis and three-layer structure in which first and second treatment units arranged in the horizontal direction are provided in the lowermost layer, third and fourth treatment units are provided above the first treatment unit in the vertical direction, and fifth and sixth treatment units are provided above the second treatment unit in the vertical direction.

The present invention will be described in detail below.

An apparatus for analyzing according to an aspect of the present invention includes at least two treatment units arranged in a vertical direction and configured to subject a sample to biochemical reaction treatment or biochemical detection treatment; and a conveying mechanism configured to convey the sample in the vertical direction and to deliver the sample from one of the treatment units to the other treatment unit. The conveying mechanism includes at least two sample conveying mechanisms configured to independently convey the sample. The sample is delivered between the two sample conveying mechanisms during conveyance.

The apparatus for analyzing according to the aspect of the present invention can have the following structures:

(1) The conveying mechanism includes a first sample conveying mechanism configured to convey the sample (for example, a pipette unit that can draw in a sample from a container and supply the sample to a different container), and a second sample conveying mechanism configured to convey the sample (for example, a container conveying robot that moves a container having a sample between the treatment units). The sample is delivered from the first sample conveying mechanism to the second sample conveying mechanism above at least one of the treatment units. This eliminates the necessity to provide an external space for delivering the sample.

(2) The conveying mechanism includes a first sample conveying mechanism configured to convey the sample (for example, the above-described pipette unit), and a second sample conveying mechanism configured to convey a container capable of holding the sample (for example, the above-described container conveying robot). The sample is delivered from the first sample conveying mechanism to the container in the treatment units. This eliminates the necessity to provide an external space for delivering the sample.

(3) The conveying mechanism includes a first sample conveying mechanism to which a pipette chip is removably attached (for example, a first pipette unit), a second sample conveying mechanism to which the pipette chip is removably attached (for example, a second pipette unit), and a pipette-chip conveying mechanism configured to convey the pipette chip (for example, a conveying robot capable of holding the pipette chip). The pipette chip is delivered from the first sample conveying mechanism to the pipette-chip conveying mechanism above at least one of the treatment units, and the delivered pipette chip is attached to the second sample conveying mechanism. This eliminates the necessity to provide an external space for delivering the sample, and reduces the number of pipette chips to be used.

(4) The conveying mechanism includes a first sample conveying mechanism to which a pipette chip is removably attached (for example, a first pipette unit), a second sample conveying mechanism to which the pipette chip is removably attached (for example, a second pipette unit), and a container conveying mechanism configured to convey a container capable of holding the pipette chip (for example, a conveying robot that conveys the pipette chip and the container). The pipette chip is delivered from the first sample conveying mechanism to the container in the treatment units, and the delivered pipette chip is attached to the second sample conveying mechanism. This eliminates the necessity to provide an external space for delivering the sample, and reduces the number of pipette chips to be used.

Exemplary embodiments of the present invention will be described in detail below with reference to the drawings.

First Exemplary Embodiment

An automatic apparatus for analyzing according to a first exemplary embodiment of the present invention will now be described. The automatic apparatus for analyzing extracts nucleic acid from a biochemical sample (for example, body fluid such as blood, body tissue, feces, urine, or phlegm), amplifies the extracted nucleic acid, subjects the amplified nucleic acid to hybridization reaction with a DNA microarray, and optically detects the reacted DNA microarray, thereby identifying a nucleic acid sequence in the biochemical sample.

Figure 2:
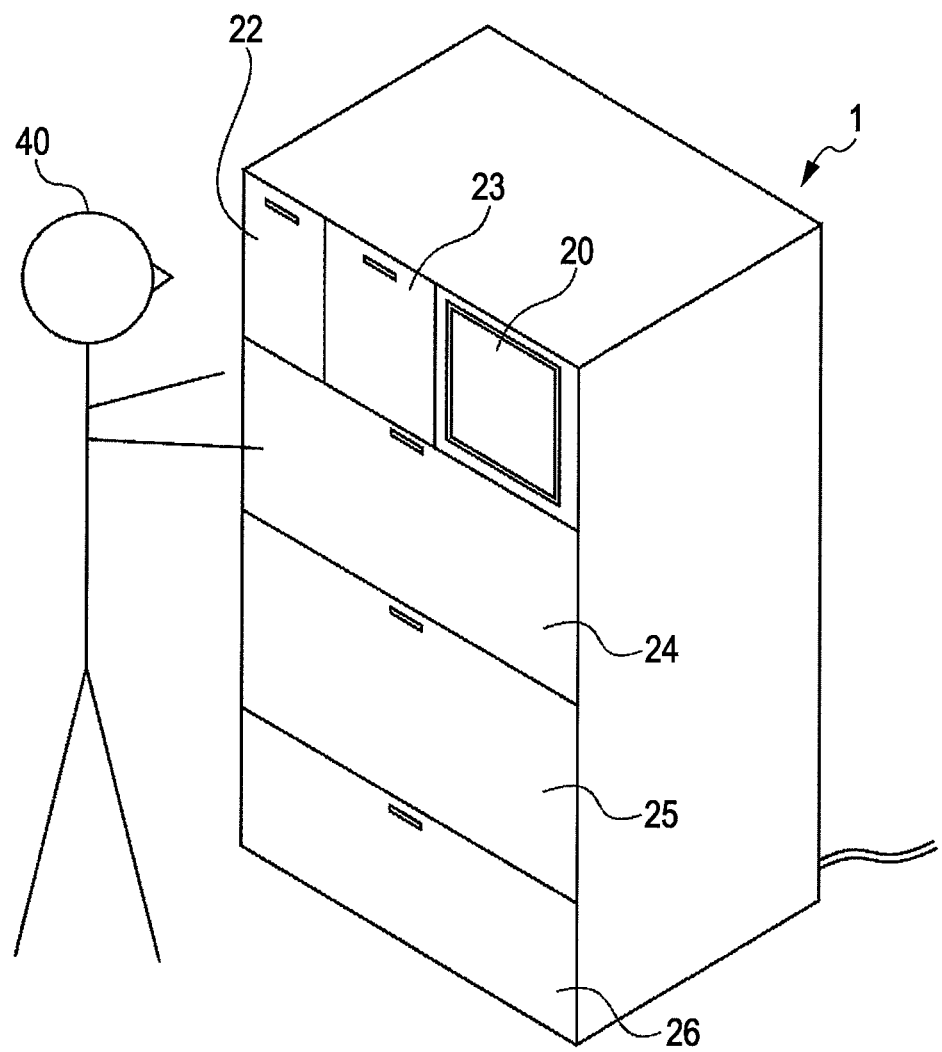
FIG. 2 is a schematic external view of the automatic apparatus for analyzing.
Figure 3:
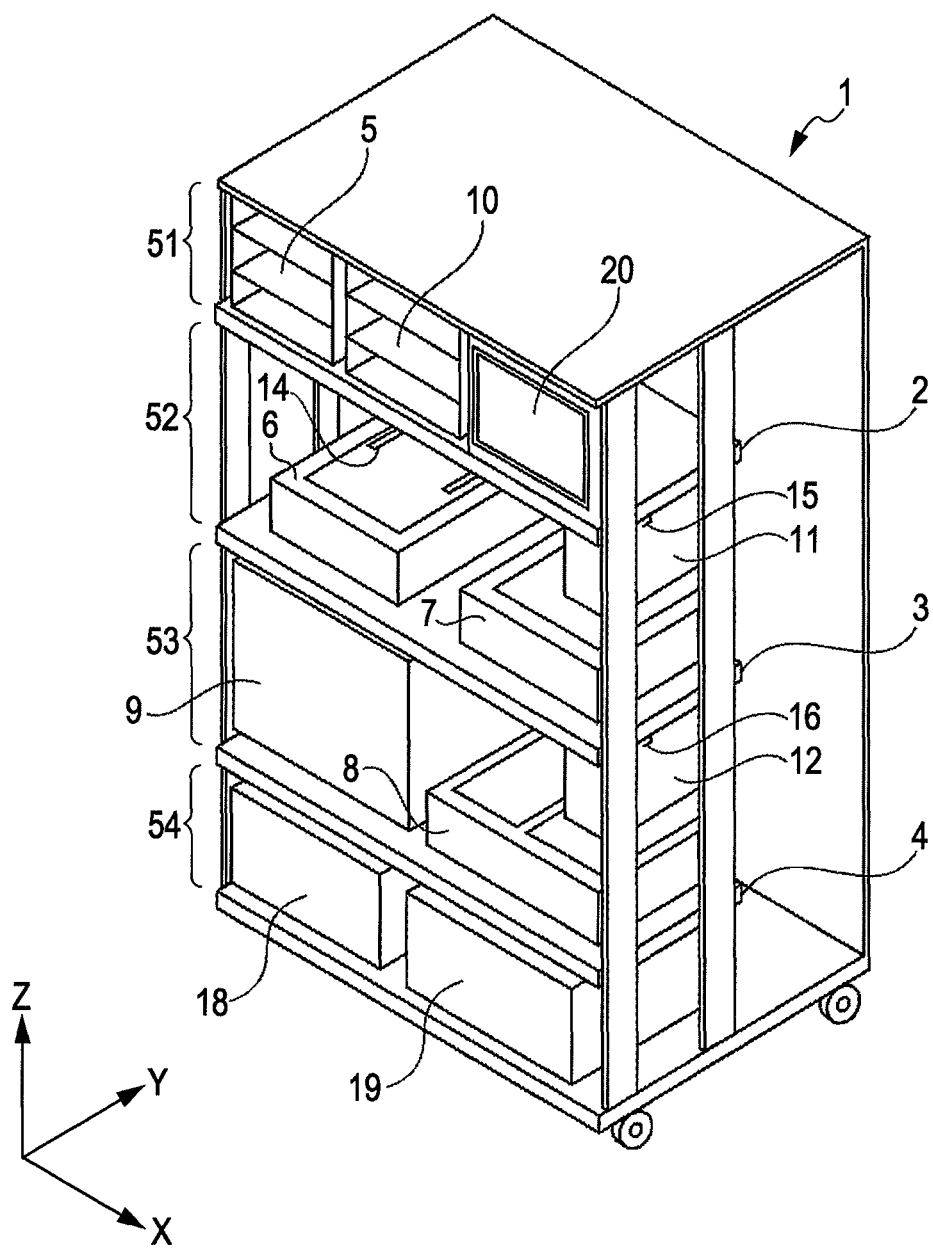
FIG. 3 is a schematic perspective view of the automatic apparatus for analyzing.
Figure 4:
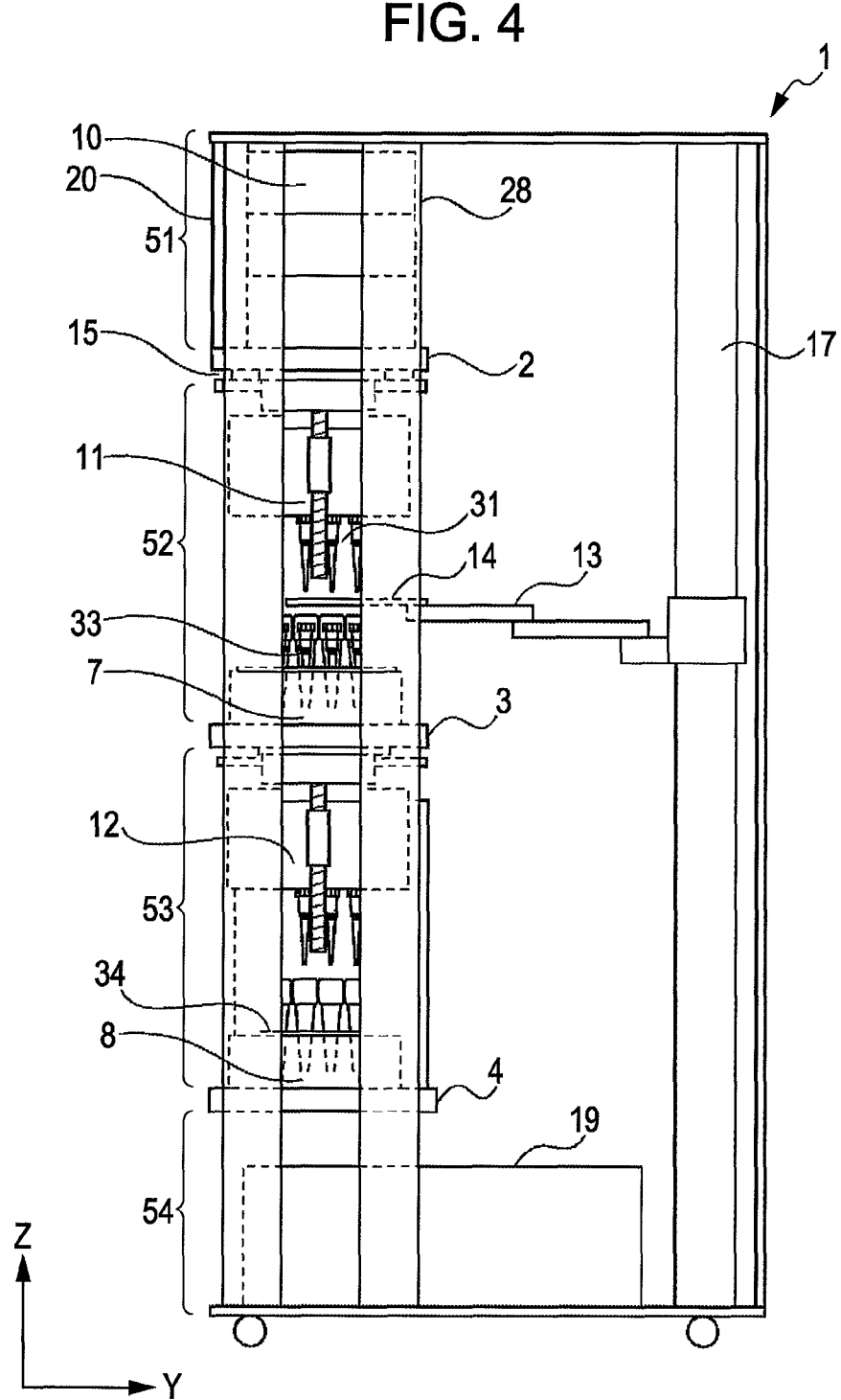
FIG. 4 is a schematic side view of the automatic apparatus for analyzing.

FIG. 1 is a schematic front view showing an internal configuration of an automatic apparatus for analyzing according to the first exemplary embodiment, and FIG. 2 is a schematic external view of the automatic apparatus for analyzing. FIGS. 3 and 4 are a perspective view and a side view, respectively, of the automatic apparatus for analyzing. In FIGS. 1, 3, and 4, a container supply unit door 22, a container recovery unit door 23, a second layer door 24, a third layer door 25, and a fourth layer door 26 are not shown for the purpose of explanation of the internal configuration.

An automatic analyzing apparatus 1 serving as the apparatus for analyzing according to the first exemplary embodiment of the present invention is of an upright type. An analysis operator 40 pulls the container supply unit door 22 open, sets a container for analysis in the automatic analyzing apparatus 1, and closes the container supply unit door 22. With the touch of an operating portion 20 formed by a touch panel, the analysis operator 40 can give operation commands, such as an analysis start command and an analysis interruption command, to the automatic analyzing apparatus 1. The operating portion 20 displays information about an attribute of a sample, analysis results, an operating condition of the apparatus, and external apparatuses. After the completion of analysis, the analysis operator 40 pulls the container recovery unit door 23 open, takes out the used container, and closes the container recovery unit door 23. The second, third, and fourth layer doors 24, 25, and 26 are provided for maintenance. For example, when an error arises in the automatic analyzing apparatus 1, the analysis operator 40 can access the interior of the automatic analyzing apparatus 1 by pulling these doors open.

The internal configuration of the automatic analyzing apparatus 1 will be described below with reference to FIGS. 1, 3, and 4.

The interior of the automatic analyzing apparatus 1 is divided into a first layer 51, a second layer 52, a third layer 53, and a fourth layer 54 in that order from above by shelf plates 2, 3, and 4.

A container supply unit 5, a container recovery unit 10, and the operating portion 20 are provided in the first layer 51.

A nucleic-acid extraction unit 6, a nucleic-acid amplification unit 7, a first pipette unit 11 serving as a first sample conveying mechanism, and an X-axis guide 15 for the first pipette unit 11 are provided in the second layer 52.

A hybridization unit 8, a DNA-microarray detection unit 9, a second pipette unit 12 serving as a second sample conveying mechanism, and an X-axis guide 16 for the second pipette unit 12 are provided in the third layer 53.

An electrical unit 18 and an auxiliary mechanical unit 19 are provided in the fourth layer 54.

Figure 5:
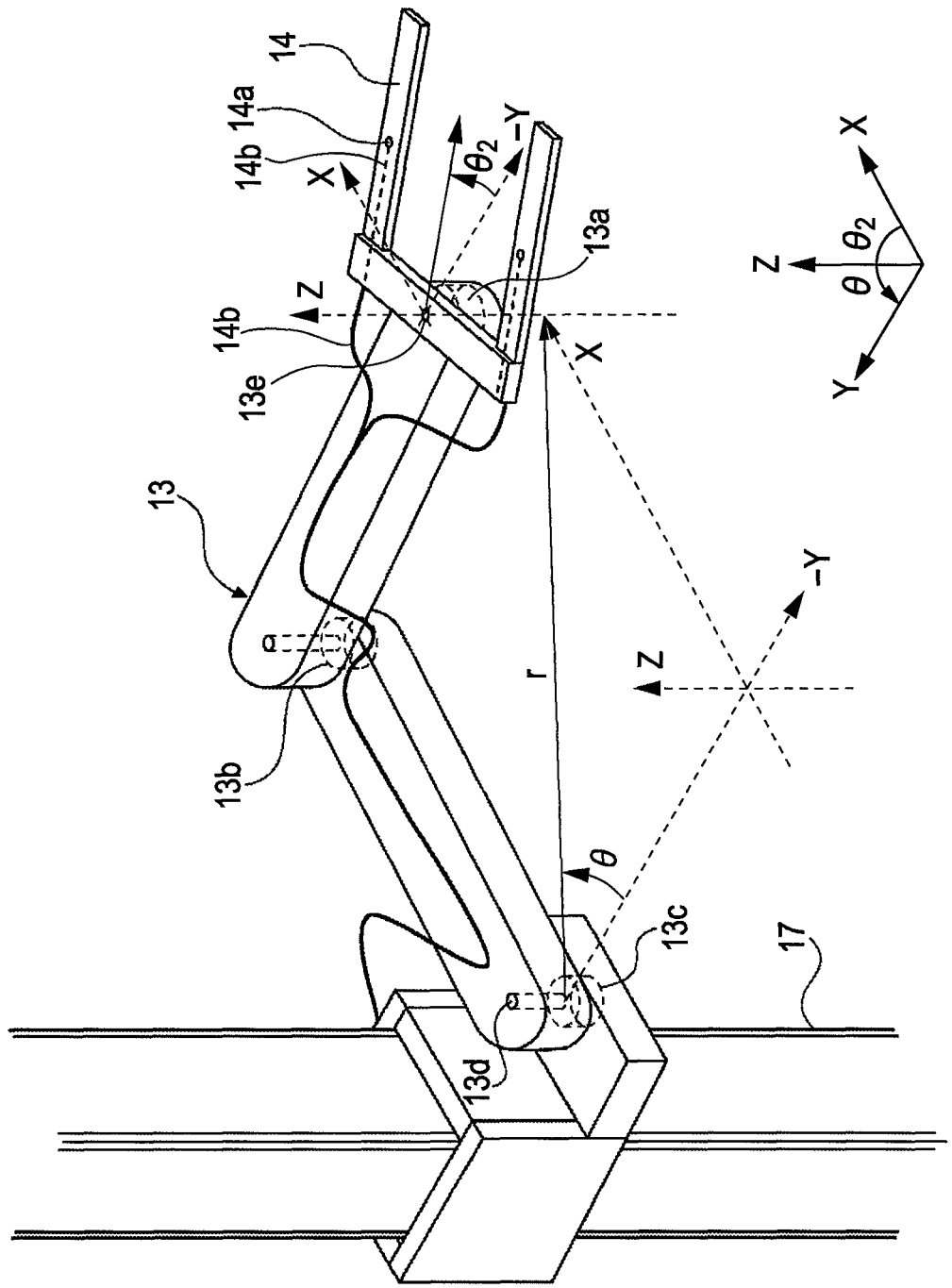
FIG. 5 is an explanatory view of a container hand in the first exemplary embodiment.

A Z-axis guide 17 for a container conveying robot vertically extends through the first to fourth layers 51 to 54. FIG. 5 shows a container conveying robot 13 serving as a container conveying mechanism. The container conveying robot 13 is movable along the Z-axis guide 17 between the first layer 51 and the fourth layer 54. At the leading end of the container conveying robot 13, a container hand 14 capable of holding each container is mounted. The container conveying robot 13 is a so-called SCARA robot that has degrees of freedom represented by the r, θ, and Z axes, that is, that makes motions in polar coordinates by using a plurality of motors. Herein, the r-axis represents the expansion length of an arm leading end portion 13e of the container conveying robot 13 relative to a base portion 13d in the XY plane, and the θ-axis represents the rotation angle of the arm leading end portion 13e relative to the base portion 13d in the XY plane. Motors 13a and 13b are provided for the r- and θ-axis motion. The container hand 14 can rotate relative to the arm leading end portion 13e in the XY plane. As shown in FIG. 5, the rotation angle of the container hand 14 in the −Y-axis direction is defined as a θ2-axis. A motor 13c is provided for the θ2-axis motion. The structure of the container conveying robot 13 is not limited to the above-described structure. For example, the container conveying robot 13 may move in the XYZ orthogonal coordinates.

The container hand 14 has holes 14a for vacuum adsorption, and the holes 14a are connected to resin tubes 14b that are connected to a vacuum pump via a valve (not shown). This structure allows switching between an ON state and an OFF state of the application of a vacuum adsorbing force.

In the first exemplary embodiment, maintenance work of the interior of the automatic analyzing apparatus 1 can be performed while the front doors are open, as described above. The Z-axis guide 17 for the container conveying robot 13 is not disposed on the front side, but is disposed on the back side for easier maintenance. If the Z-axis guide 17 is disposed on the right or left side of the automatic analyzing apparatus 1, the container conveying robot 13 is required to have a long stroke in the X-axis direction, and it is difficult to ensure a conveying path. For the above-described reasons, that is, in order to improve the maintenance ability, to prevent the increase in stroke of the container conveying robot 13, and to easily ensure the conveying path, the Z-axis guide 17 is disposed in almost the back center of the automatic analyzing apparatus 1.

Structures of a container 33 for amplification of nucleic acid and a container 34 for storing hybridization reagent will now be described with reference to FIGS. 6 and 7.

Figure 6:
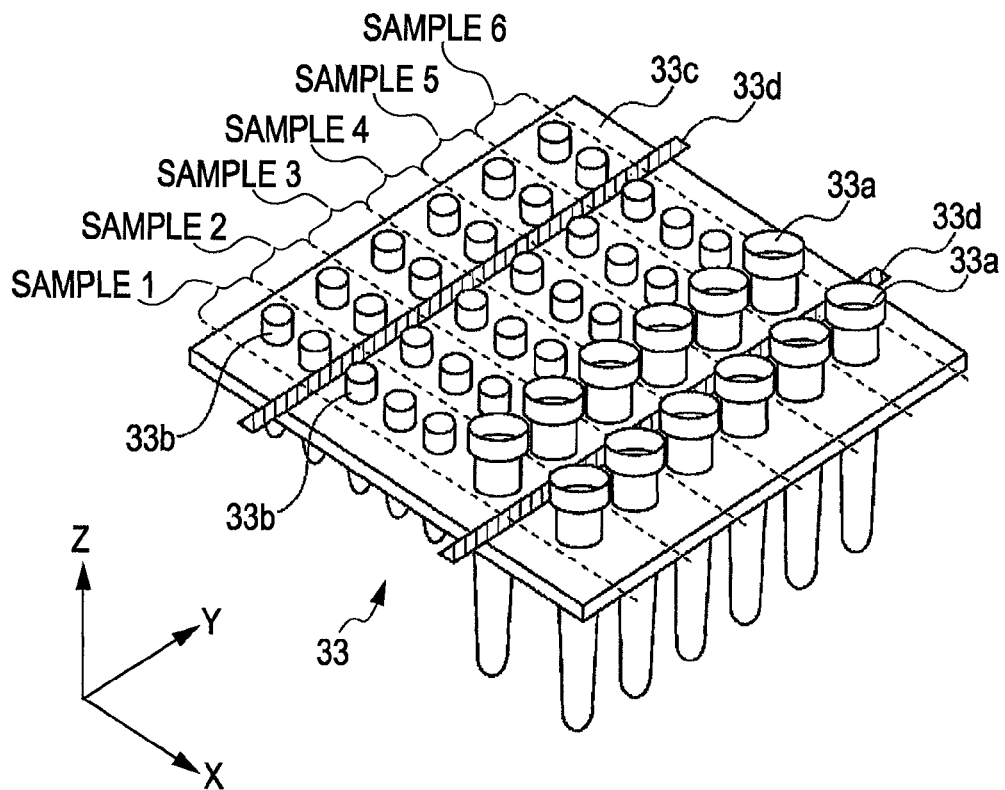
FIG. 6 is an explanatory view of a container for amplification of nucleic acid in the first exemplary embodiment.

FIG. 6 is a perspective view of the container 33 for amplification of nucleic acid. The container 33 for amplification of nucleic acid is substantially shaped like a well plate, and includes a plate portion 33c. One row in the container 33 extending in the X-axis direction can be used for reaction of one sample. While the container 33 for amplification of nucleic acid in the first exemplary embodiment is ready for six samples, it can be designed in accordance with the specifications of the apparatus. A pipette chip 31 can be stored in each recess 33a for storing the pipette chip 31. The pipette chip 31 can be automatically loaded in a pipette unit while being stored in the recess 33a. In order to prevent a leading end of the pipette chip 31 from deforming during loading, a stepped portion provided in an upper part of the recess 33a is shaped so as to be in contact with a narrow portion near the neck of the pipette chip 31. Liquid wells 33b can hold a reagent and samples according to a reaction protocol in the amplification process. The pitch in the Y-direction of the recesses 33a and the liquid wells 33b is the same as the pitch of the pipette chips 31 attached to the first pipette unit 11 and the second pipette unit 12. The container 33 for amplification of nucleic acid is held at areas 33d by the container hand 14.

Figure 7:
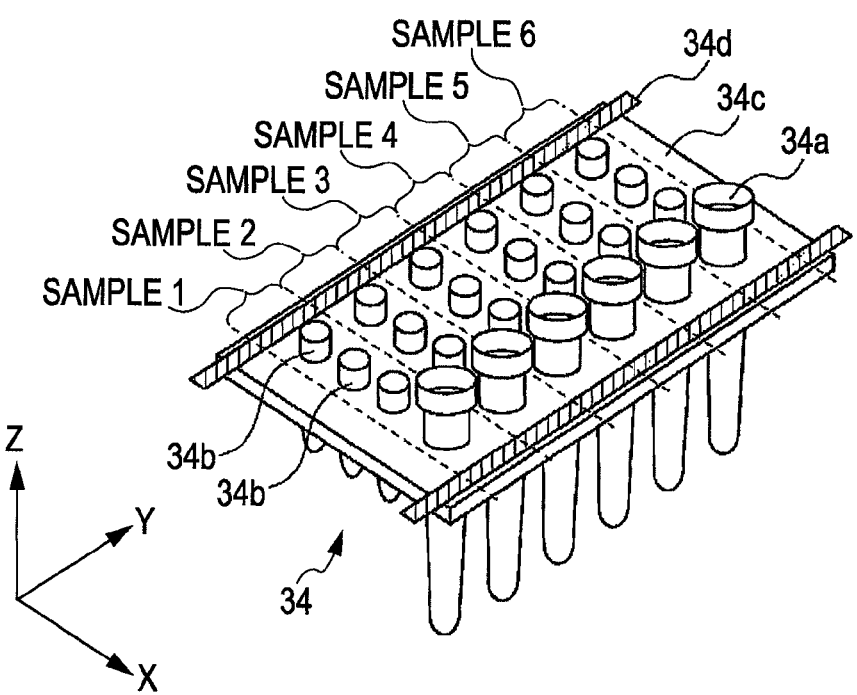
FIG. 7 is an explanatory view of a container for storing hybridization reagent in the first exemplary embodiment.

The container 34 for storing hybridization reagent shown in FIG. 7 has a structure similar to that of the container 33 for amplification of nucleic acid, and includes recesses 34a for storing pipette chips, liquid wells 34b, a plate portion 34c, and areas 34 to be held by the container hand 14. The X-direction distance between the two areas 34d is the same as the X-direction distance between the two areas 33d in the container 33 for amplification of nucleic acid. For this reason, the container 33 for amplification of nucleic acid and the container 34 for storing hybridization reagent can be held by the same container hand 14.

In order to convey the container 33 for amplification of nucleic acid, the container hand 14 comes from the −Y-direction to the +Y-direction in FIG. 6, and holds the container 33. In the first exemplary embodiment, the container hand 14 is placed below the plate portion 33c, and a lower surface of the plate portion 33c is vacuum-adsorbed by an upper surface of the container hand 14. Holding may be performed by other known methods, for example, mechanical chucking, magnetic attraction, a friction method using the container's own weight, and electrostatic attraction. However, in Step S304 in FIG. 30 that will be described below, the container 33 for amplification of nucleic acid, the container hand 14, the container conveying robot 13, and the Z-axis guide 17 for the container conveying robot 13 receive a downward force from the second pipette unit 12. Therefore, it is necessary to make design so that displacement between the container hand 14 and the container 33 for amplification of nucleic acid and plastic deformation of the mechanical components are not caused by the downward force.

Figure 8:
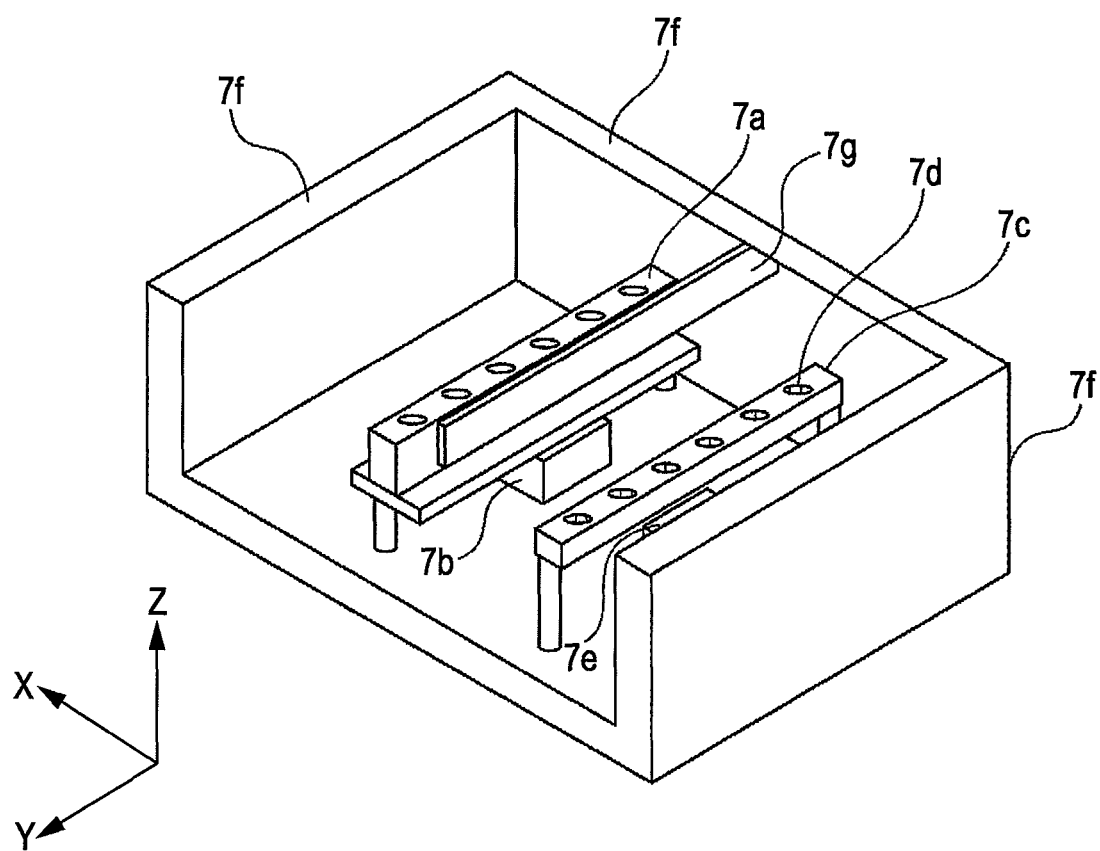
FIG. 8 is a perspective view of a nucleic-acid amplification unit in the first exemplary embodiment.
Figure 9:
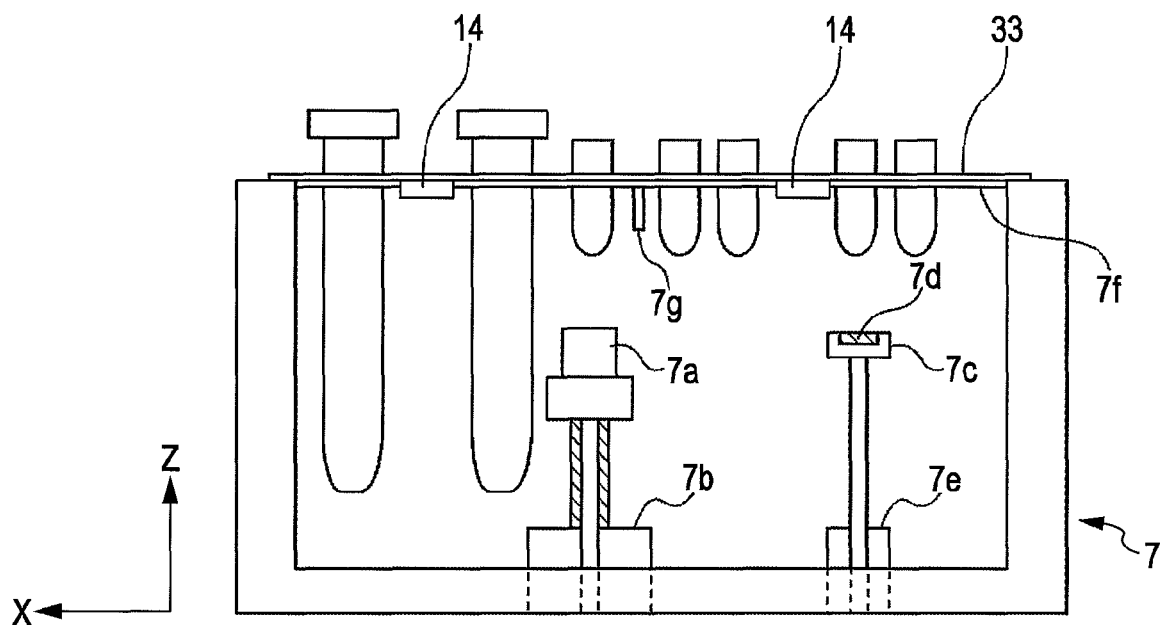
FIG. 9 is a rear sectional view showing a state in which the container for amplification of nucleic acid is placed in the nucleic-acid amplification unit in the first exemplary embodiment.

FIG. 8 is a perspective view of the nucleic-acid amplification unit 7, and FIG. 9 is a front sectional view showing a state in which the container 33 for amplification of nucleic acid is placed in the nucleic-acid amplification unit 7. In FIG. 8, a thermal block 7a controls the temperature of liquid in the wells for PCR. A Peltier element (not shown) is used as a temperature control actuator. The thermal block 7a is driven in the Z-axis direction by a motor 7b. In order to bring the wells into contact with the thermal block 7a, the motor 7b is driven so that the thermal block 7a moves up in the +Z-direction. In this case, the container 33 for amplification of nucleic acid is fixed by a clamp mechanism (not shown) so as not to lift. A magnetic plate 7c is used for purification of nucleic acid using magnetic beads. The magnetic plate 7c is formed by bonding permanent magnets 7d to a non-magnetic plate member. The magnetic plate 7c is driven in the Z-direction by a Z-actuator 7e. A peripheral portion 7f receives an outer edge portion of the container 33 for amplification of nucleic acid. In a state in which the container 33 for amplification of nucleic acid is placed in the nucleic-acid amplification unit 7, the container hand 14 can come from the −Y-direction into a cutout for the container hand 14. For this reason, the container hand 14 can hold the container 33 for amplification of nucleic acid from below the plate portion 33c.

Figure 10:
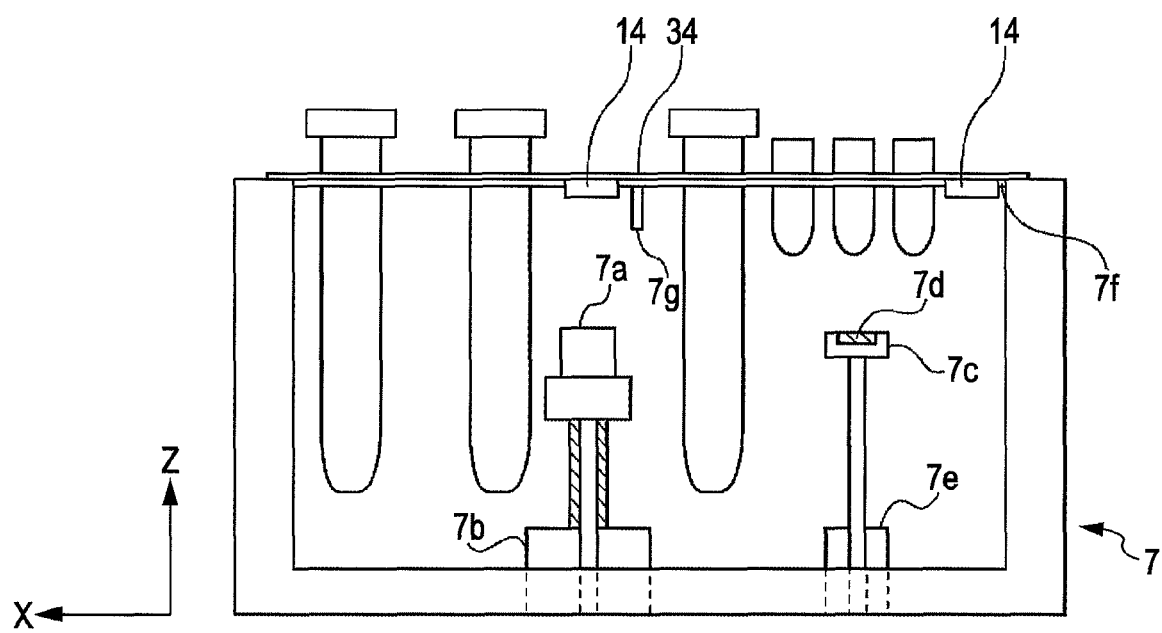
FIG. 10 is a rear sectional view showing a state in which the container for storing hybridization reagent is placed in the nucleic-acid amplification unit in the first exemplary embodiment.

The above-described structure of the nucleic-acid amplification unit 7 can be easily designed so that both the container 33 for amplification of nucleic acid and the container 34 for storing hybridization reagent can be placed therein. Similarly, the structure of the container hand 14 can be easily designed so as to hold both the container 33 for amplification of nucleic acid and the container 34 for storing hybridization reagent. Referring to FIGS. 8 to 10, in order to overcome the width difference in the X-direction between the container 33 for amplification of nucleic acid and the container 34 for storing hybridization reagent, a support member 7g of the nucleic-acid amplification unit 7 supports the container 34 for storing hybridization reagent. The heat block 7a and the magnetic plate 7c are arranged so as not to interfere with the container 34 for storing hybridization reagent.

The components will be described below in line with the flow of analysis.

For analysis, the analysis operator 40 first sets a container 32 for extraction of nucleic acid, a container 33 for amplification of nucleic acid, a container 34 for storing hybridization reagent, and a DNA microarray cassette 35 in the container supply unit 5.

Then, the container hand 14 holds the container 32 for extraction of nucleic acid set in the container supply unit 5, and the container conveying robot 13 is driven in the r, θ, and Z axes and conveys the container 32 to the nucleic-acid extraction unit 6. Subsequently, the container hand 14 sequentially holds and conveys the container 33 for amplification of nucleic acid, the container 34 for storing hybridization reagent, and the DNA microarray cassette 35 to the nucleic-acid amplification unit 7, the hybridization unit 8, and the hybridization unit 8, respectively.

The container 32 for extraction of nucleic acid is conveyed to the nucleic-acid extraction unit 6. Prior to analysis, a sample, a reagent, and pipette chips are put in the container 32 outside the automatic analyzing apparatus 1. Nucleic acid can be extracted from a biochemical sample by known methods. While the first exemplary embodiment adopts a method using magnetic silica beads, for example, a column method, a centrifuge separation method, an electrophoresis method, and a nanopillar method are also applicable to extraction of nucleic acid according to the present invention.

The first pipette unit 11 is moved to recesses provided in the container 32 for extraction of nucleic acid by the X-axis guide 15 for the first pipette unit 11 and a Z-axis driving mechanism, and attaches pipette chips 31 stored in the recesses to a lower end thereof. Subsequently, the first pipette unit 11 mixes the reagent and the sample in the container 32 for extraction of nucleic acid. When a predetermined process for extraction of nucleic acid is completed, the samples (extracted nucleic-acid products) are held in wells provided in the container 32 for extraction of nucleic acid. If the analysis operator 40 does not want to carry over the samples and the reagent adhering to the pipette chips 31 during the nucleic-acid extraction process, the pipette chips 31 can be replaced with new ones. The used pipette chips can be put into the recesses for storing pipette chips provided in container 32 for extraction of nucleic acid.

As described above, the container 33 for amplification of nucleic acid is conveyed to the nucleic-acid amplification unit 7. Prior to analysis, a reagent and pipette chips are put in the container 33 outside the automatic analyzing apparatus 1.

FIGS. 8 and 9 are rear views showing the structure of the nucleic-acid amplification unit 7. The nucleic-acid amplification unit 7 includes a heat block 7a for PCR, a motor 7b for driving the heat block 7 along the Z-axis, a magnetic plate 7c having magnets 7d, and an actuator 7e for driving the magnetic plate 7c along the Z-axis. The nucleic-acid amplification unit 7 also includes a peripheral portion 7f on which the container 33 for amplification of nucleic acid is placed, and a support member 7g on which the container 34 for storing hybridization reagent is placed. The container hand 14 enters the nucleic-acid amplification unit 7 from the rear side of the automatic analyzing apparatus 1. For that purpose, a rear side member of the nucleic-acid amplification unit 7 has a large cutout. FIG. 9 shows a state in which the container hand 14 enters the nucleic-acid amplification unit 7 and holds the container 33 for amplification of nucleic acid from below.

After the process for extraction of nucleic acid, the first pipette unit 11 moves the samples (extracted nucleic-acid products) from the container 32 for extraction of nucleic acid in the nucleic-acid extraction unit 6 to the container 33 for amplification of nucleic acid in the nucleic-acid amplification unit 7. After the extracted nucleic-acid products are moved, the container 32 for extraction of nucleic acid is conveyed to the container recovery unit 10 while being held by the container hand 14.

Nucleic acid in the extracted nucleic-acid products can be amplified by known methods. While the first exemplary embodiment adopts PCR (polymerase chain reaction), for example, LCR (ligase chain reaction) and isothermal amplification are also applicable to amplification of nucleic acid in the present invention. After the target nucleic acid is exponentially amplified by PCR, purification of nucleic acid is performed by using magnetic beads in order to remove the reagent, and the target nucleic acid is labeled with a fluorescent substance. Purification of nucleic acid can be performed not only by a magnetic bead method, but also by a column filter method, a centrifuge separation method, an electrophoresis method, and a nanopillar method (see Japanese Patent Laid-Open No. 2004-045357). Labeling of the target nucleic acid with the fluorescent substance is performed by bonding a fluorescent substance to the target by PCR using bonded primer nucleic acid. Labeling can also be performed by other methods in accordance with the detection method, for example, by bonding microparticles, and by performing labeling by an intercalator method during hybridization. Since methods for observing bonding between the target and the probe without labeling have been proposed, the labeling process can be omitted by using these methods.

As described above, the container 34 for storing hybridization reagent and the DNA microarray cassette 35 are conveyed to the hybridization unit 8. A reagent is put in the container 34 for storing hybridization reagent beforehand outside the automatic analyzing apparatus 1. Also, a DNA microarray is put in the DNA microarray cassette 35 beforehand outside the automatic analyzing apparatus 1.

The samples which have been subjected to nucleic-acid amplification process (labeled and amplified products, hereinafter simply referred to as "amplified products") are drawn from the container 33 for amplification of nucleic acid by the first pipette unit 11. Then, the container 34 for storing hybridization reagent is conveyed above the container 33 for amplification of nucleic acid while being held by the container hand 14. In this state, the amplified products in the first pipette unit 11 are discharged into the container 34 for storing hybridization reagent. Subsequently, the pipette chips 31 attached to the first pipette unit 11 are transferred into the container 34 for storing hybridization reagent, and the container 34 for storing hybridization reagent is conveyed from the nucleic-acid amplification unit 7 to the hybridization unit 8. After that, the container 33 for amplification of nucleic acid is conveyed to the container recovery unit 10 while being held by the container hand 14.

The amplified products and the hybridization reagent are mixed and arranged in the container 34 for storing hybridization reagent by the second pipette unit 12, thus preparing a hybridization sample solution. The hybridization sample solution in the container 34 for storing hybridization reagent is put into the DNA microarray cassette 35 by the second pipette unit 12. For example, by keeping the temperature in the DNA microarray cassette 35 at a predetermined temperature of 45° C. to 60° C. for a predetermined period of ten minutes to four hours, hybridization reaction is caused between the target nucleic acid and the nucleic acid probe on the substrate. In this case, the hybridization sample solution in the DNA microarray cassette 35 can be moved by a liquid stirring mechanism (not shown). After the completion of hybridization reaction, a cleaning liquid provided in any of the liquid wells of the container 34 for storing hybridization reagent is put into the DNA microarray cassette 35, and allowed to flow. This improves the hybridization selectivity. After cleaning, an air flow is formed by taking air into the DNA microarray cassette 35 with a negative pressure mechanism (not shown), and the DNA microarray cassette 35 is dried by the air flow.

When the hybridization process is completed, the DNA microarray cassette 35 is conveyed to the DNA microarray detection unit 9 while being held by the container hand 14. Further, the container 34 for storing hybridization reagent is conveyed to the container recovery unit 10 while being held by the container hand 14.

The DNA microarray detection unit 9 includes at least an illumination light source, an optical sensor, and an optical element that are not shown. These components are provided in a space shielded from external light. By irradiating the DNA microarray with illumination light, the fluorescent substance in the fluorescently labeled target nucleic acid bonded to the nucleic acid probe on the DNA microarray is excited so as to produce fluorescence. The fluorescence is read by the optical sensor.

When the detection process is completed, the DNA microarray cassette 35 is conveyed from the detection unit 9 to the container recovery unit 10 while being held by the container hand 14. The analysis operator 40 manually takes the container 32 for extraction of nucleic acid, the container 33 for amplification of nucleic acid, the container 34 for storing hybridization reagent, and the DNA microarray cassette 35 out of the container recovery unit 10, and disposes of these containers.

In the automatic analyzing apparatus 1 according to the first exemplary embodiment, the treatment units for the process for extraction of nucleic acid, the process for amplification of nucleic acid, the hybridization process, and the DNA microarray detection process are provided independently. Therefore, the treatment units can treat different inspection lots of samples.

Figure 11:
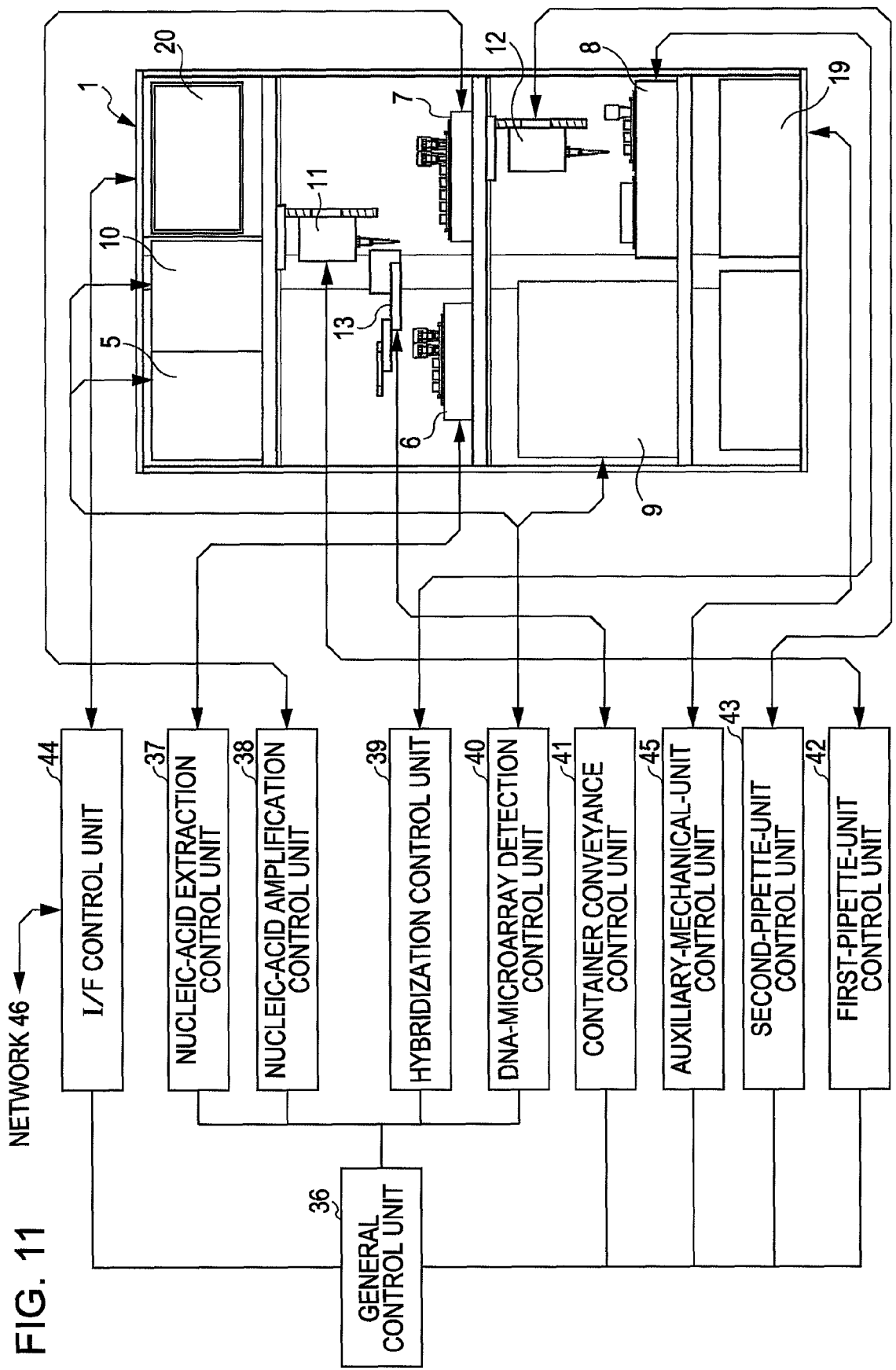
FIG. 11 is a control block diagram of the automatic apparatus for analyzing according to the first exemplary embodiment.

FIG. 11 is a control block diagram of the automatic analyzing apparatus 1 according to the first exemplary embodiment. A general control unit 36 exerts sequence control over the entire automatic analyzing apparatus 1, and uses a central processing unit (CPU). The general control unit 36 communicates with nine control subunits, that is, a nucleic-acid extraction control unit 37, a nucleic-acid amplification control unit 38, a hybridization control unit 39, a DNA microarray detection control unit 40, a container conveyance control unit 41, a first-pipette-unit control unit 42, a second-pipette-unit control unit 43, an I/F control unit 44, and an auxiliary-mechanical-unit control unit 45. Communication operations include transmission of operation commands and reception of detected states. Each subunit controls the input and output of signals from and to the actuators and sensors. The general control unit 36 is connected to an external network 46 via the I/F control unit 44 so as to communicate with an external apparatus (not shown). For example, the general control unit 36 has a function of exchanging data with an electronic medical chart system.

A method for delivering the liquid from the second layer 52 to the third layer 53 will now be described in detail with reference to FIGS. 12 to 28.

Figure 12:
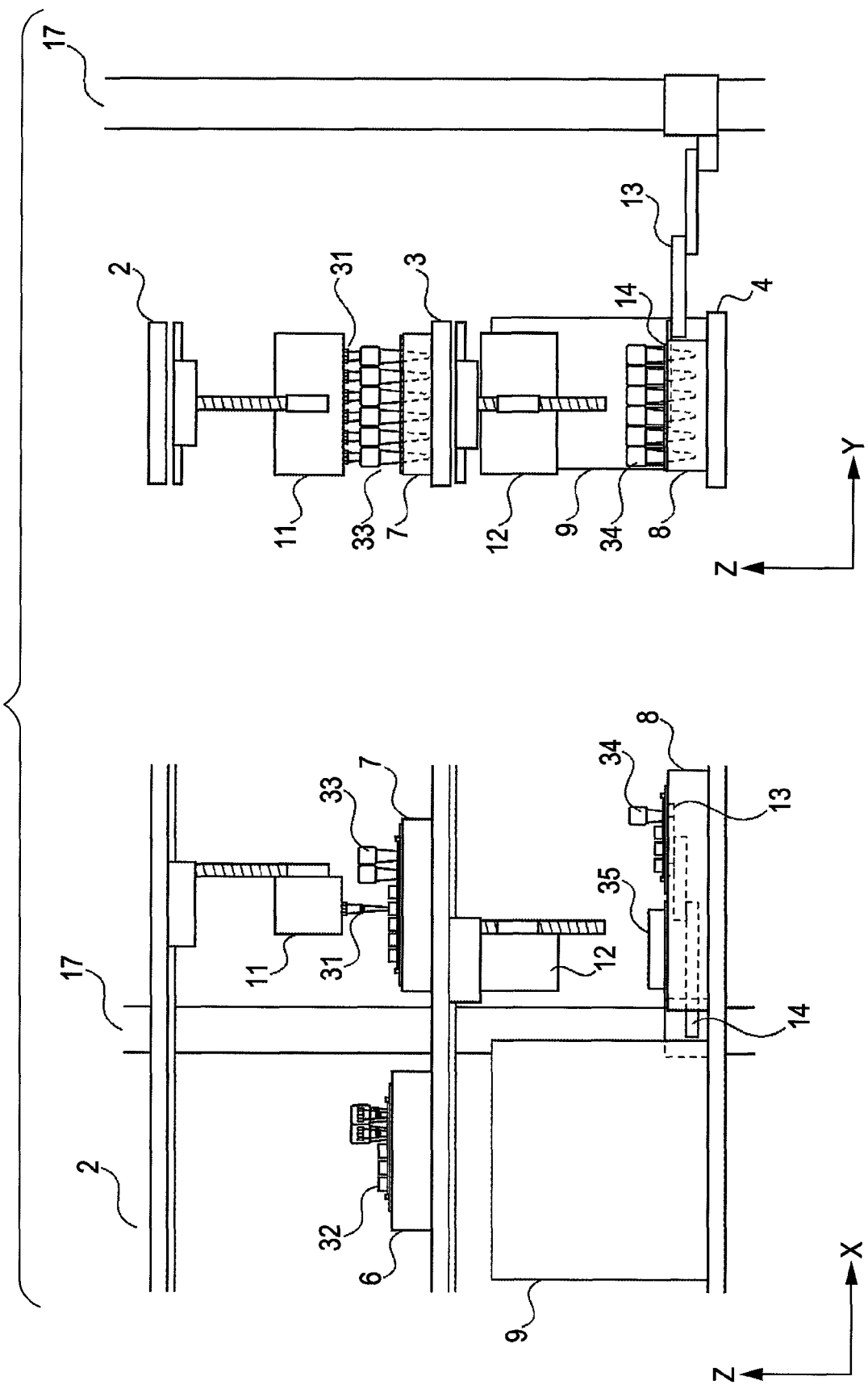
FIG. 12 is an explanatory view showing an operation of delivering liquid and pipette chips in the automatic apparatus for analyzing.
Figure 13:
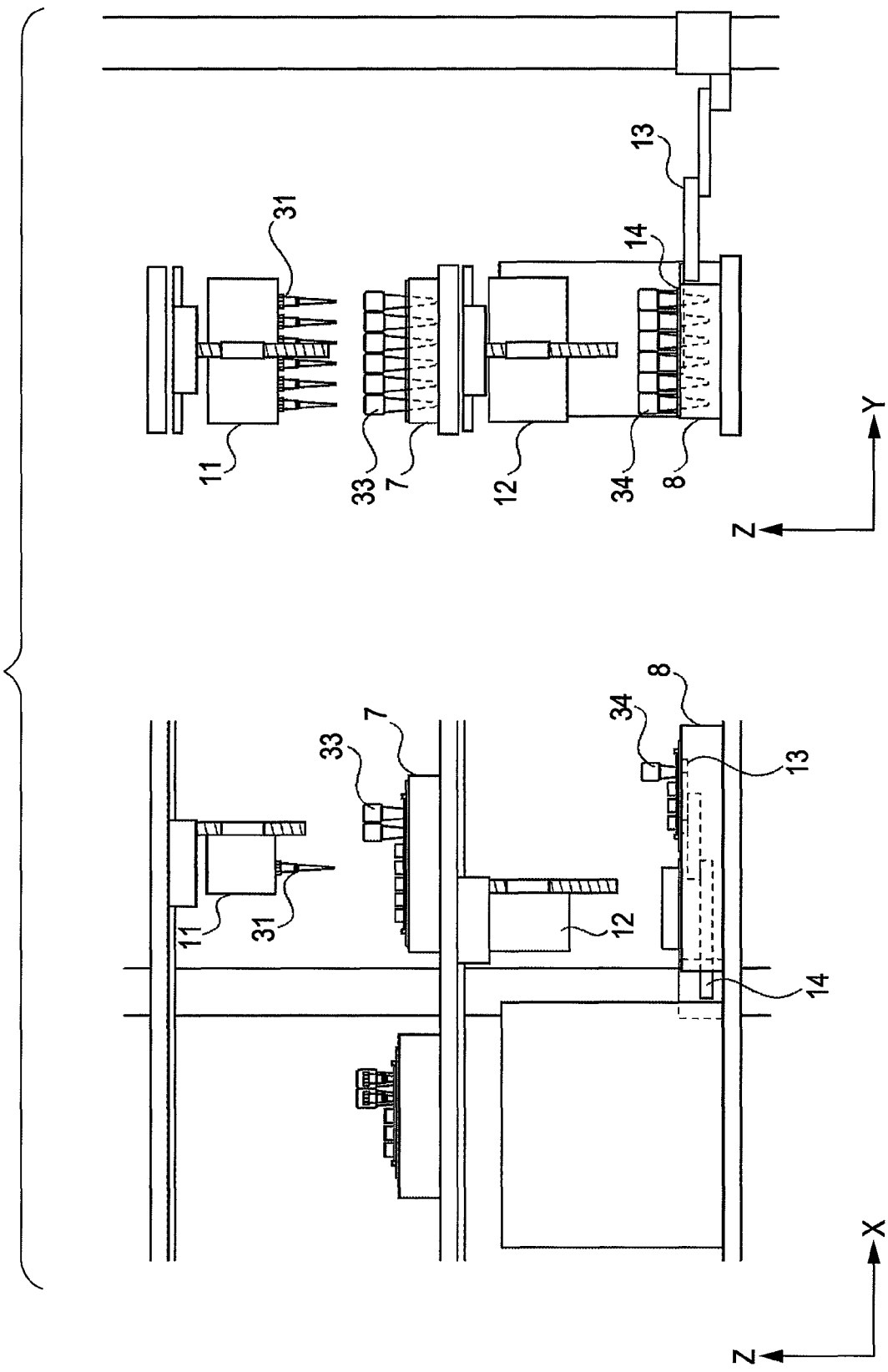
FIG. 13 is an explanatory view showing the operation of delivering the liquid and the pipette chips in the automatic apparatus for analyzing.
Figure 14:
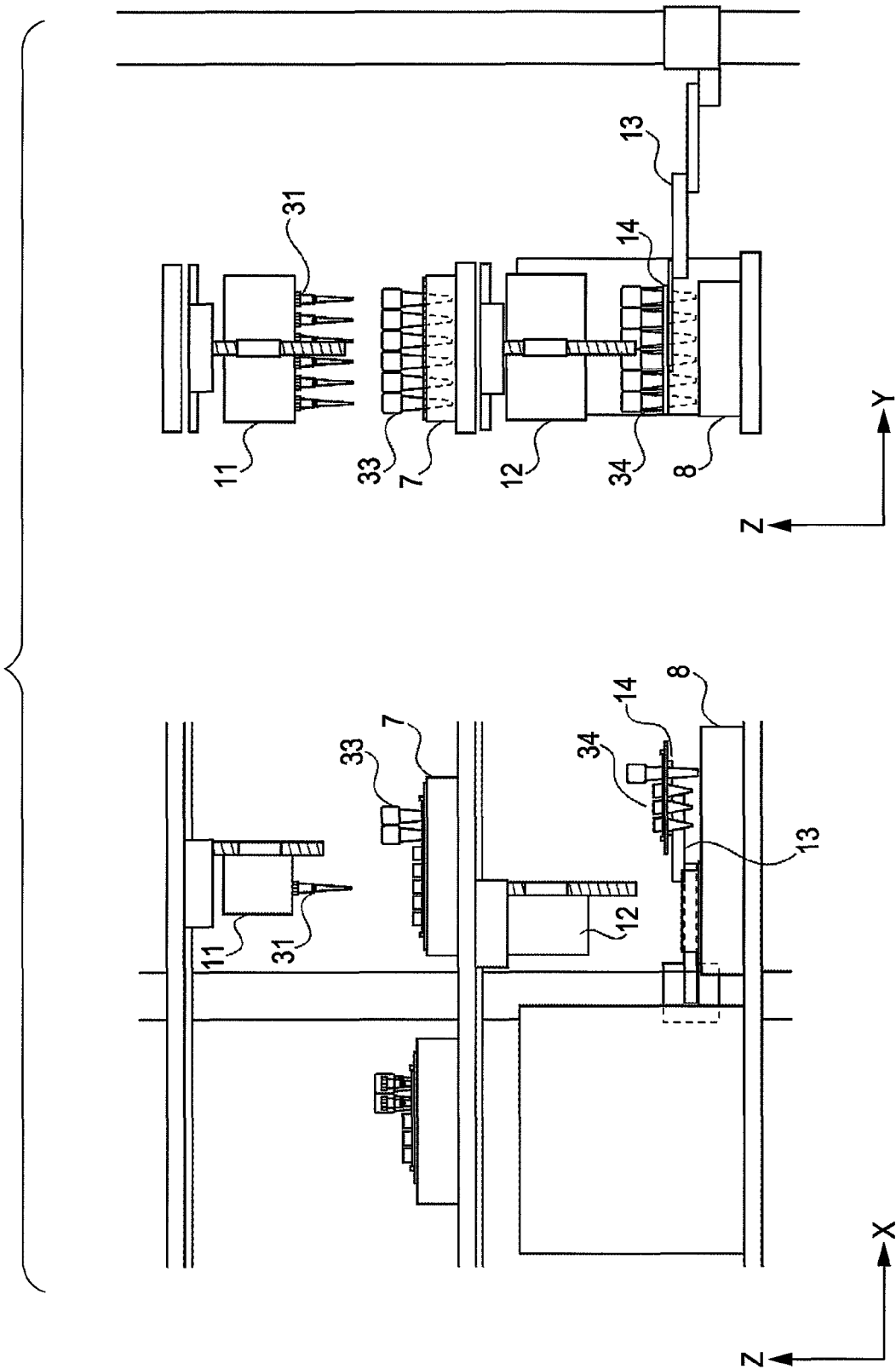
FIG. 14 is an explanatory view showing the operation of delivering the liquid and the pipette chips in the automatic apparatus for analyzing.
Figure 15:
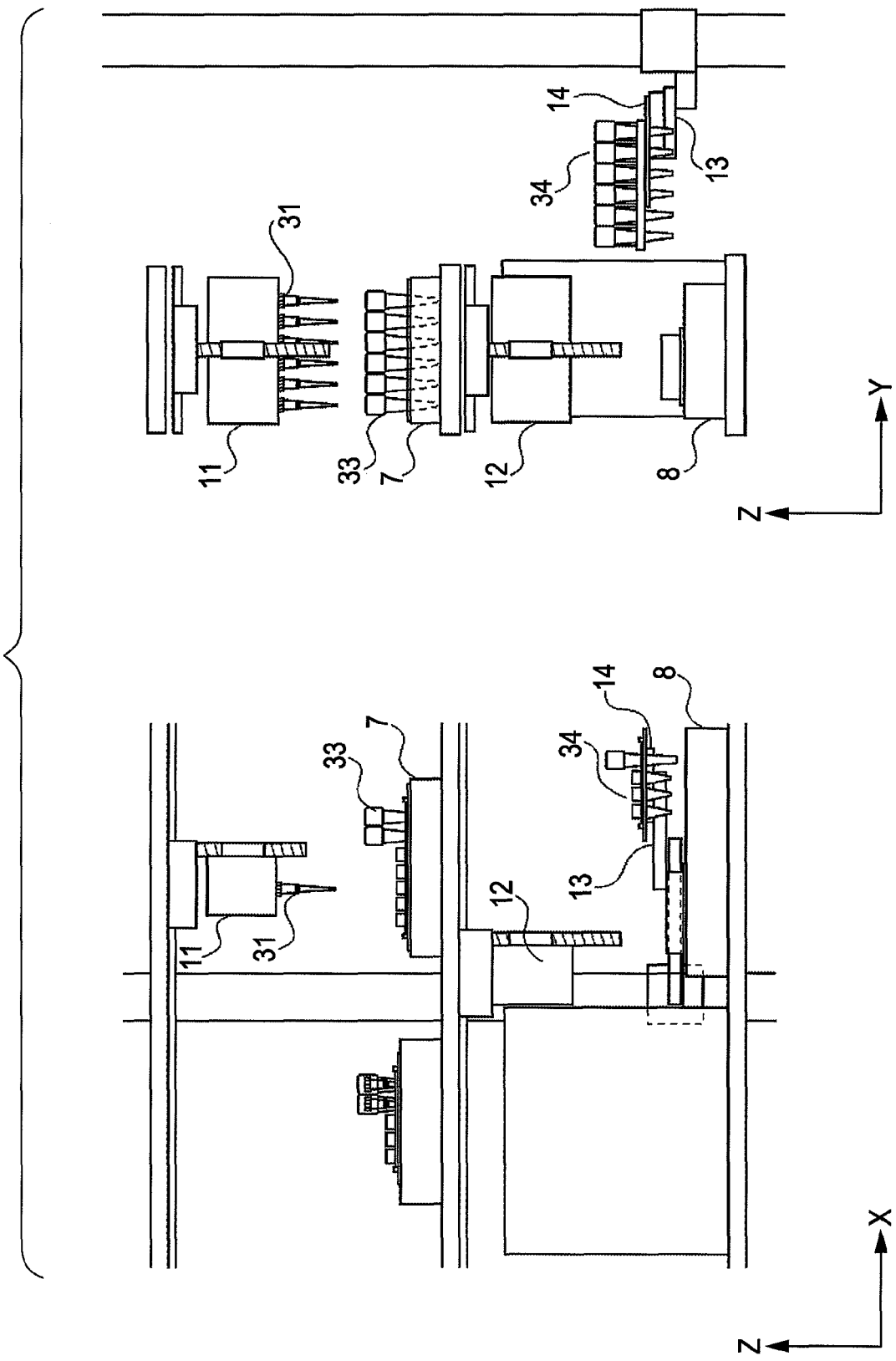
FIG. 15 is an explanatory view showing the operation of delivering the liquid and the pipette chips in the automatic apparatus for analyzing.
Figure 16:
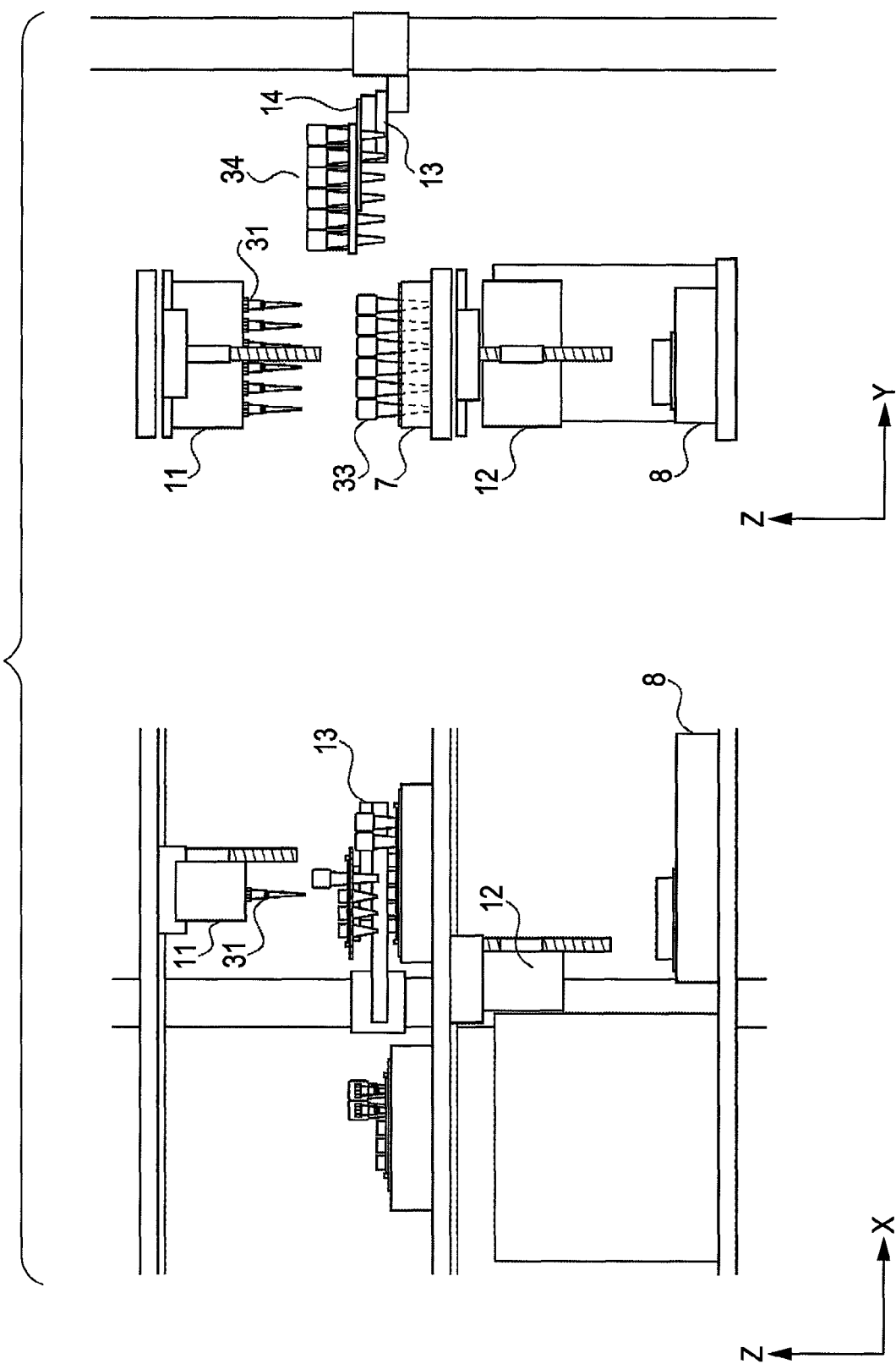
FIG. 16 is an explanatory view showing the operation of delivering the liquid and the pipette chips in the automatic apparatus for analyzing.
Figure 17:
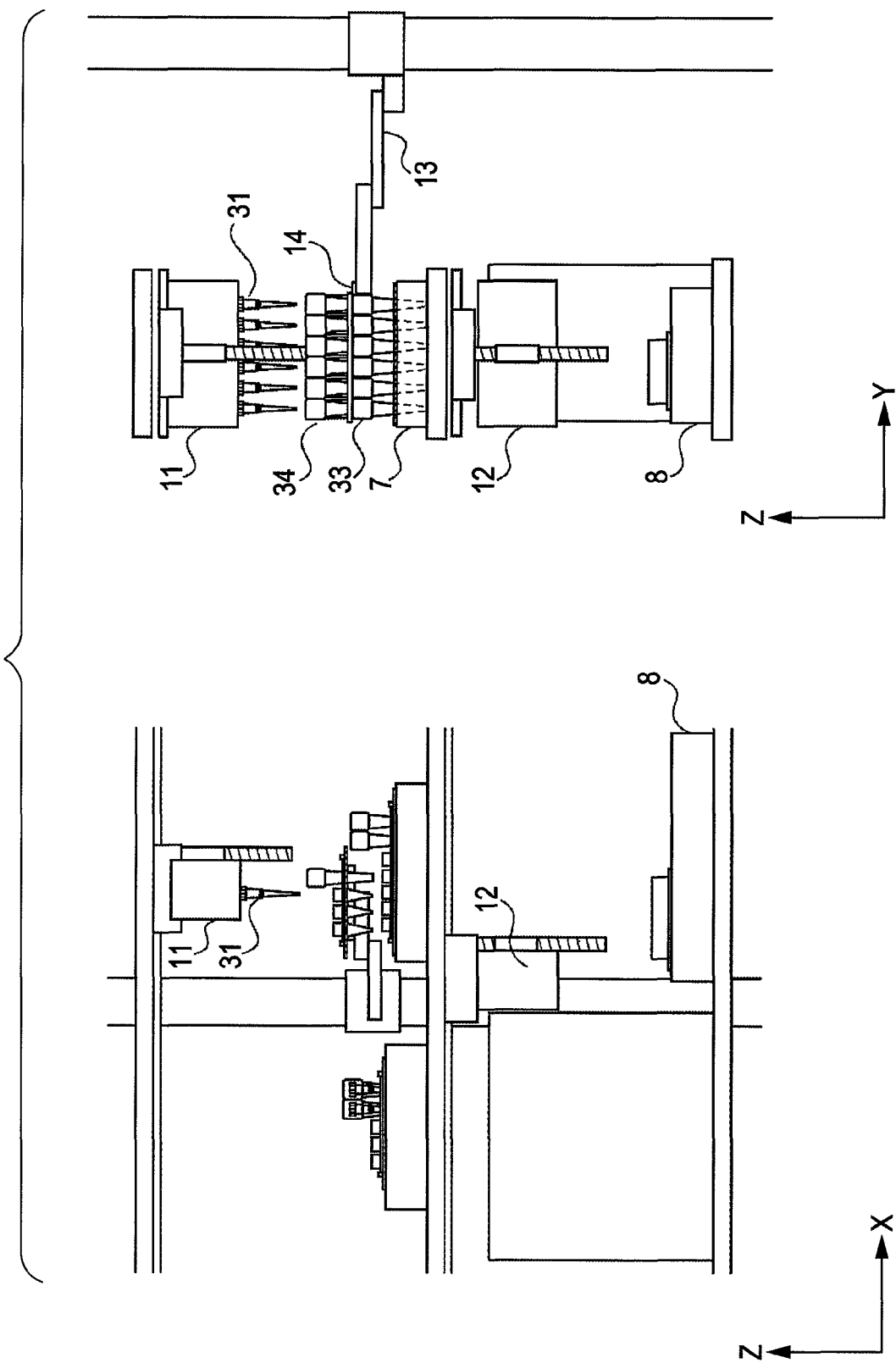
FIG. 17 is an explanatory view showing the operation of delivering the liquid and the pipette chips in the automatic apparatus for analyzing.
Figure 18:
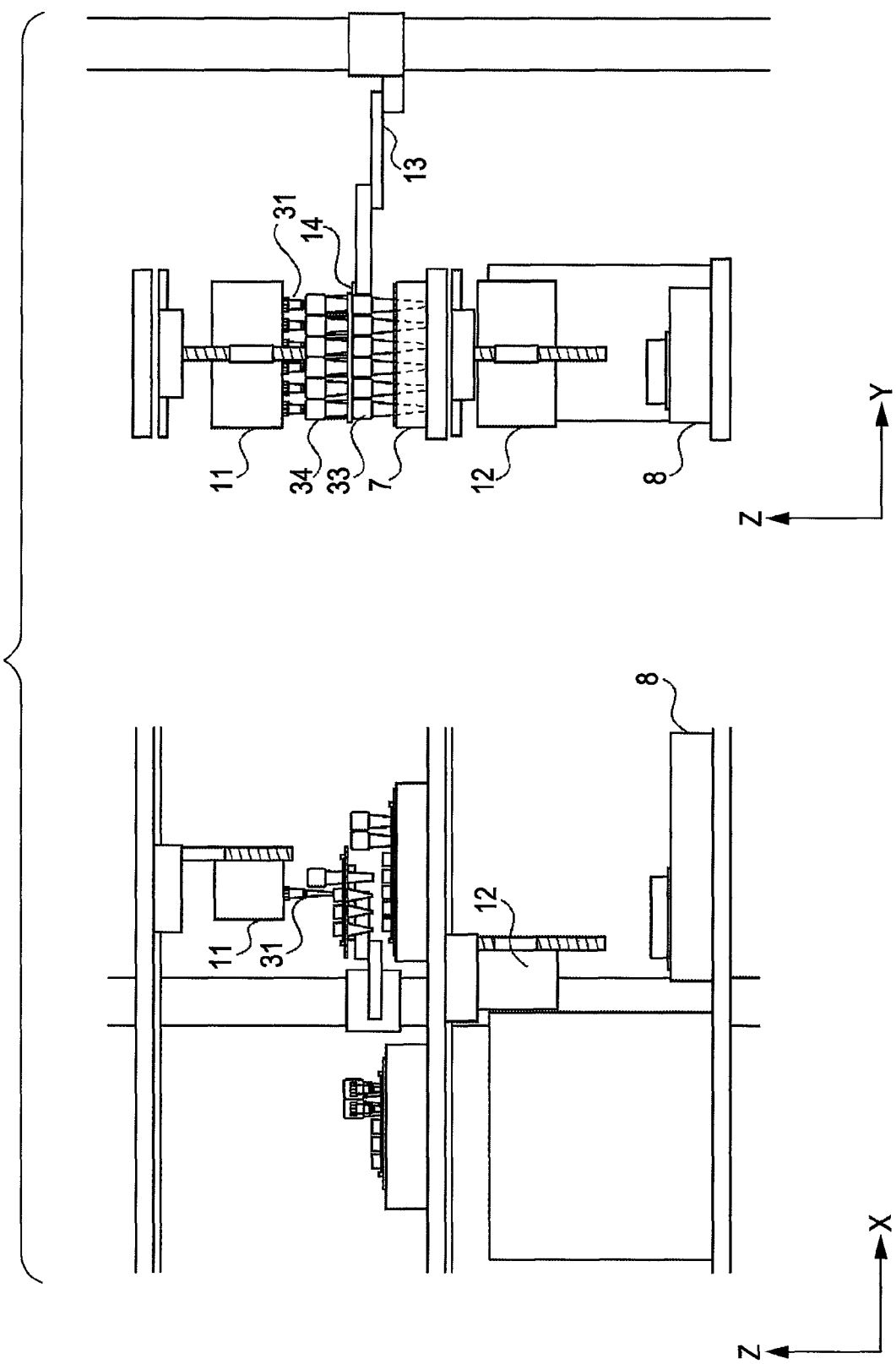
FIG. 18 an explanatory view showing the operation of delivering the liquid and the pipette chips in the automatic apparatus for analyzing.
Figure 19:
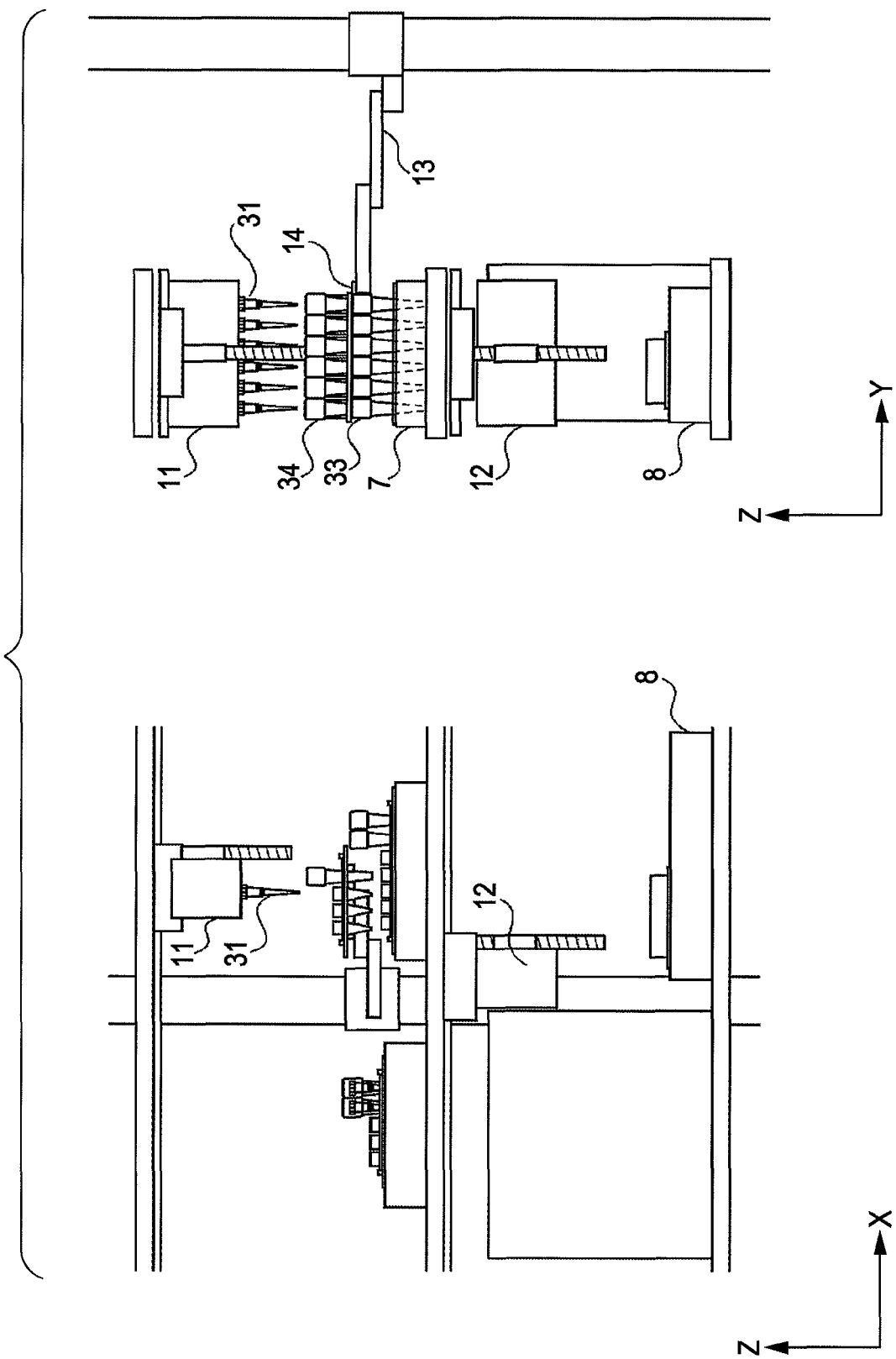
FIG. 19 is an explanatory view showing the operation of delivering the liquid and the pipette chips in the automatic apparatus for analyzing.
Figure 20:
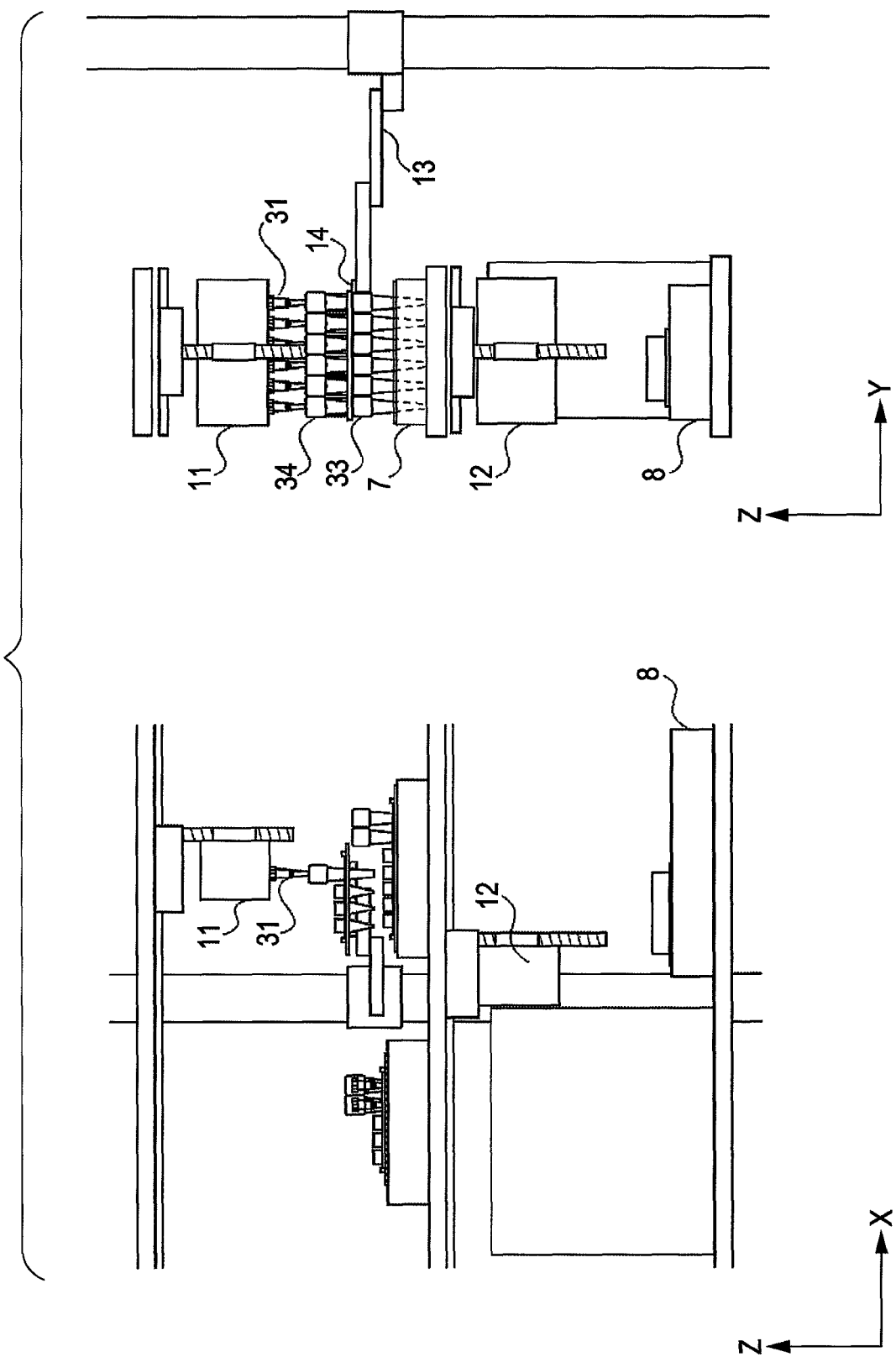
FIG. 20 is an explanatory view showing the operation of delivering the liquid and the pipette chips in the automatic apparatus for analyzing.
Figure 21:
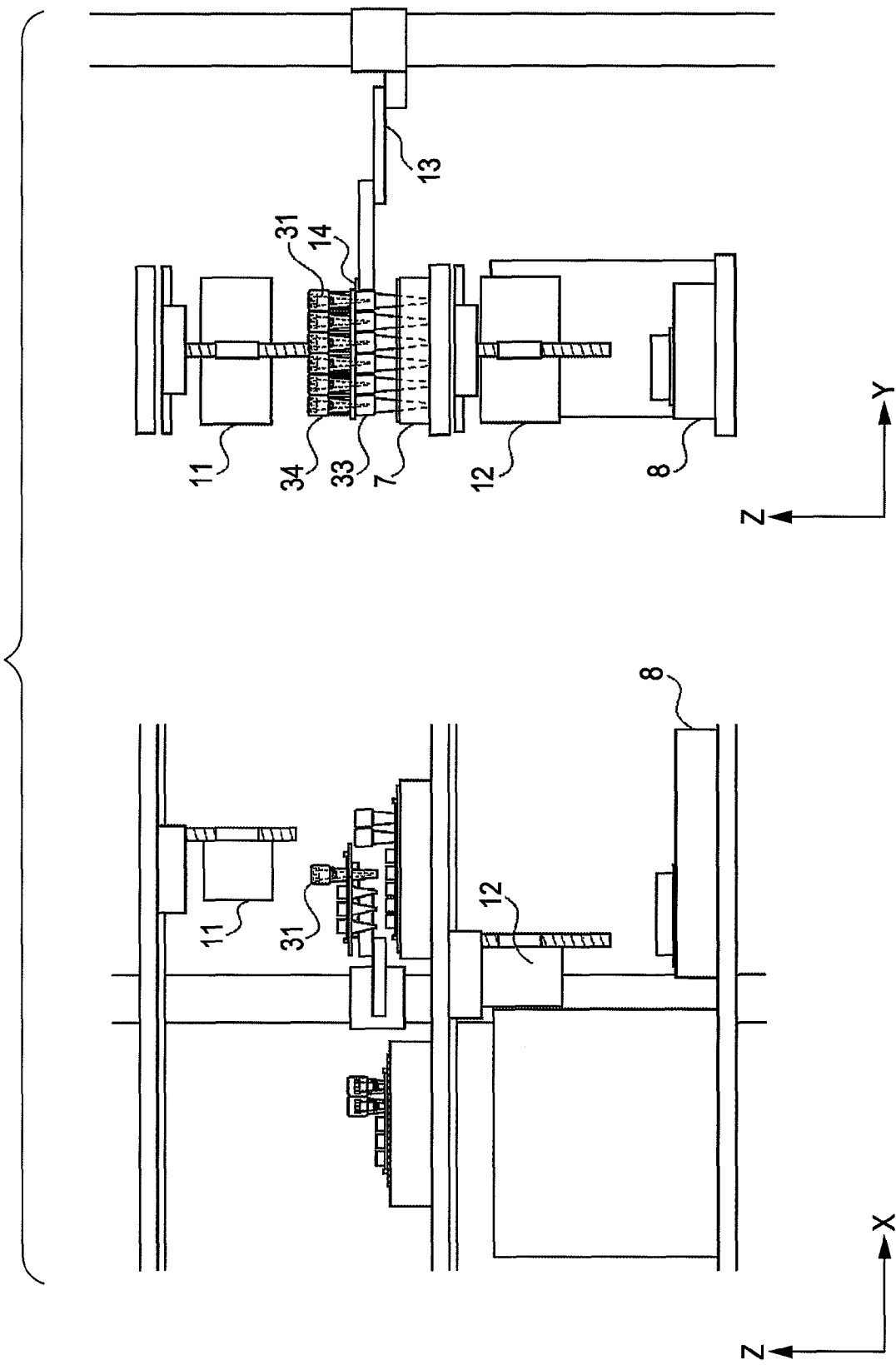
FIG. 21 is an explanatory view showing the operation of delivering the liquid and the pipette chip in the automatic apparatus for analyzing.
Figure 22:
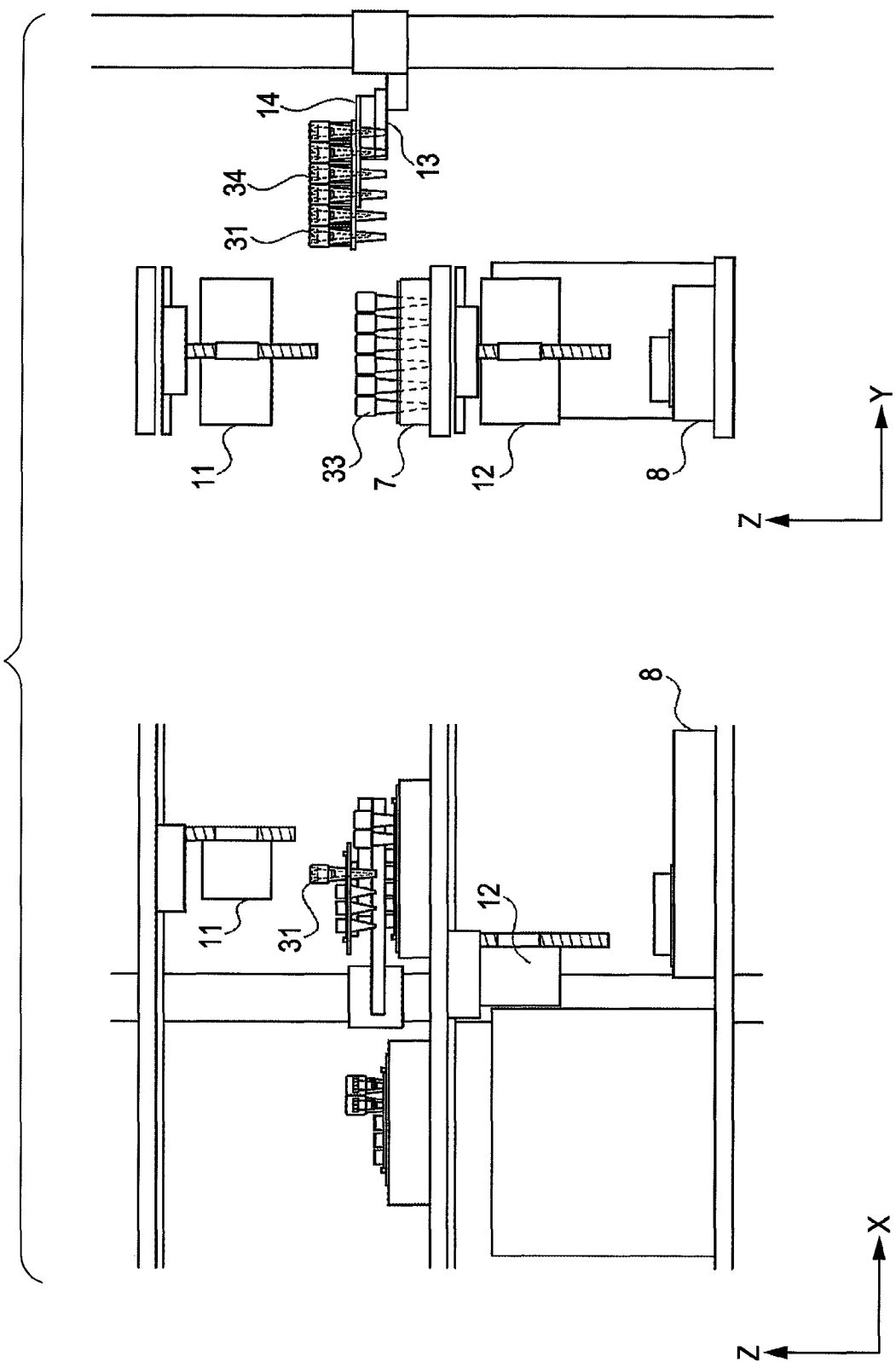
FIG. 22 is an explanatory view showing the operation of delivering the liquid and the pipette chips in the automatic apparatus for analyzing.
Figure 23:
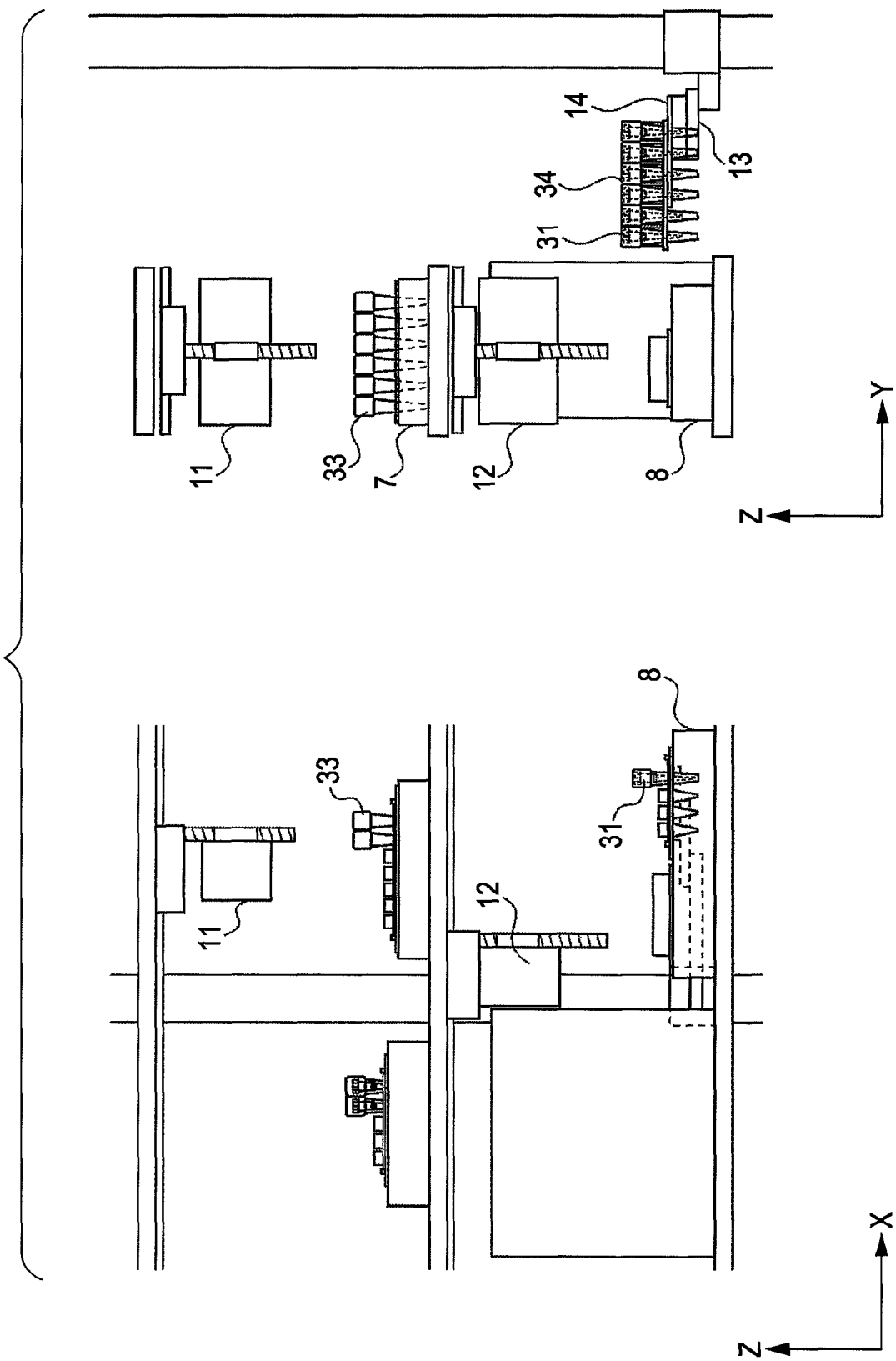
FIG. 23 is an explanatory view showing the operation of delivering the liquid and the pipette chips in the automatic apparatus for analyzing.
Figure 24:
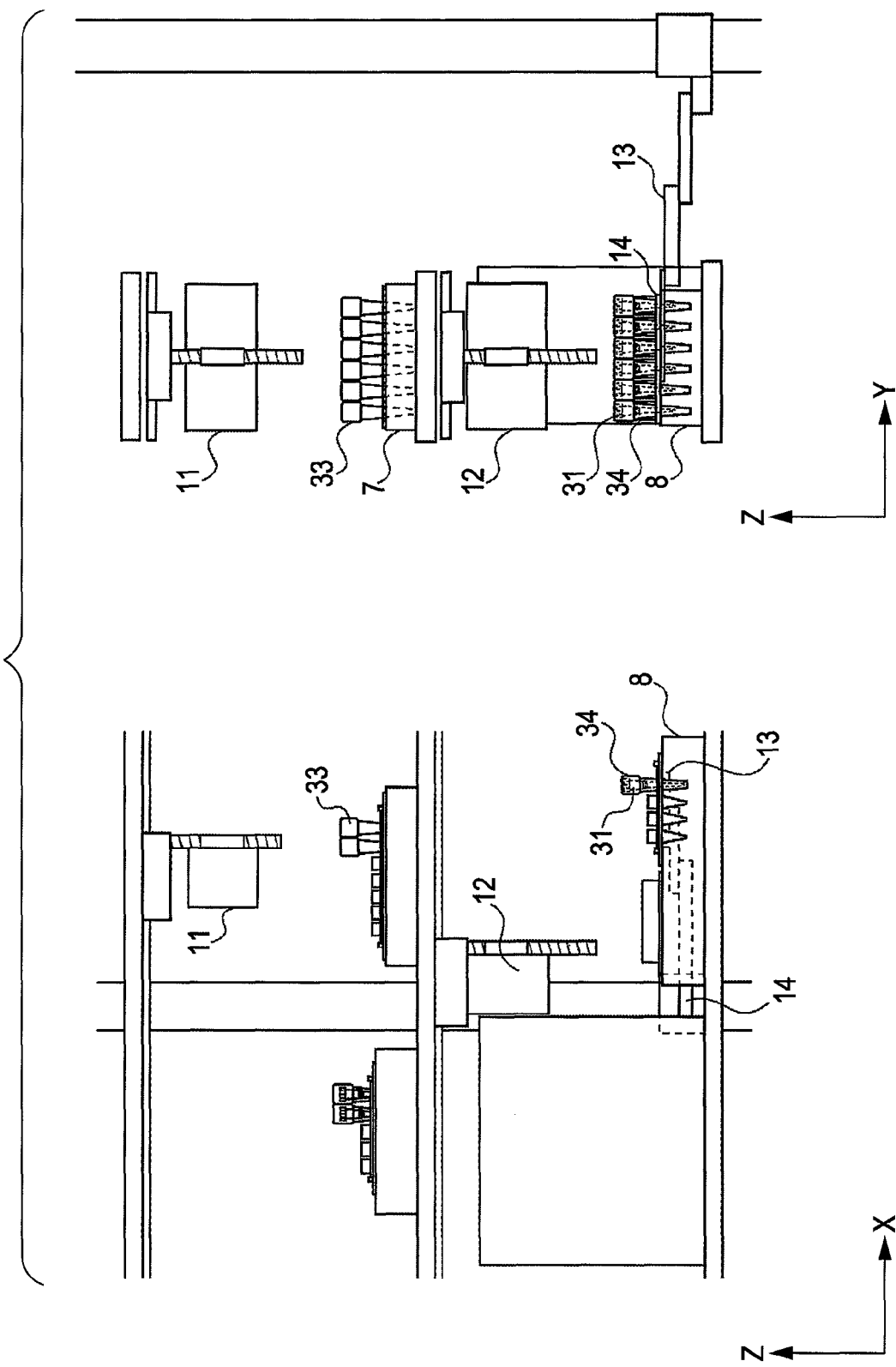
FIG. 24 is an explanatory view showing the operation of delivering the liquid and the pipette chip in the automatic apparatus for analyzing.
Figure 25:
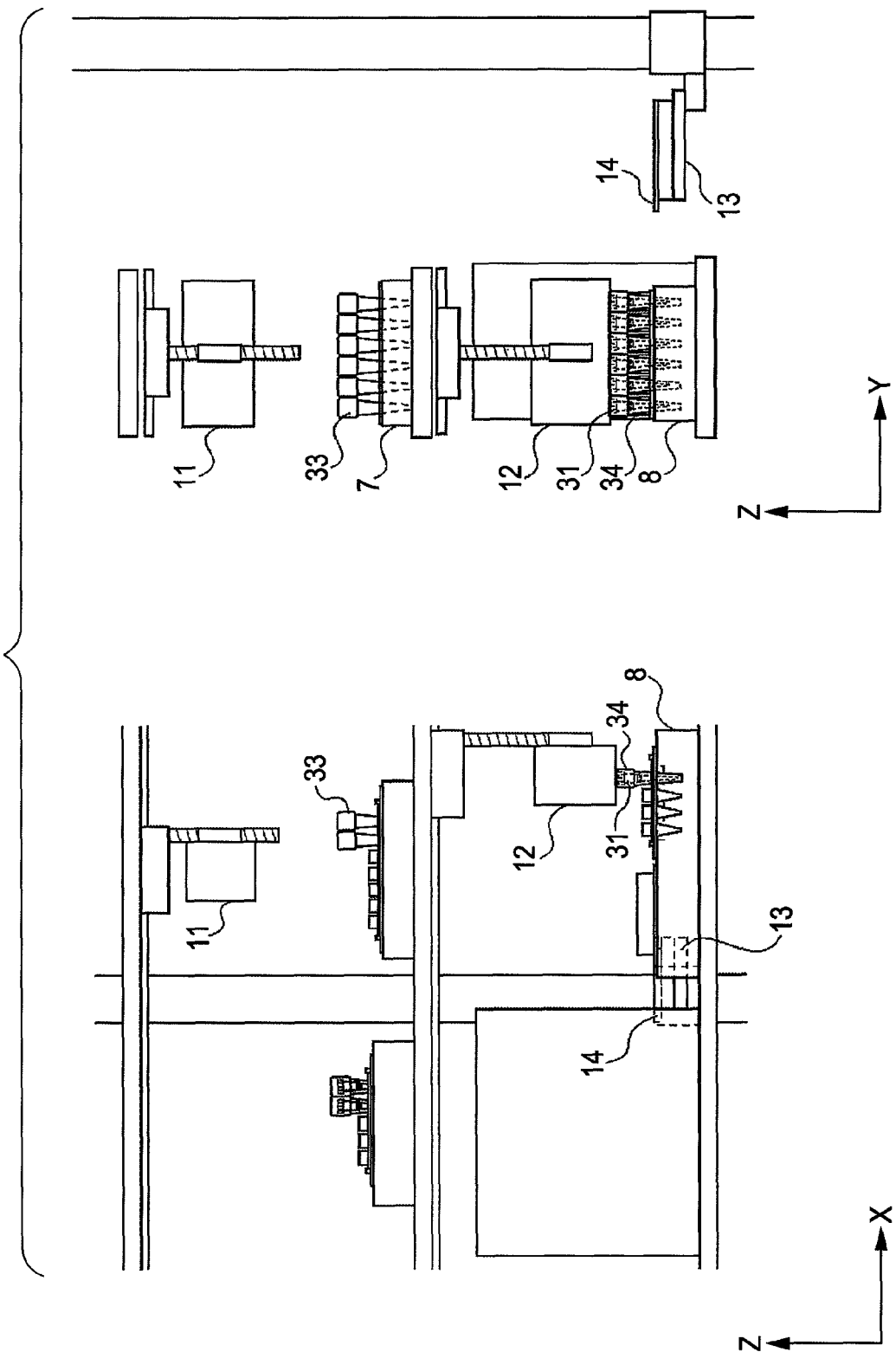
FIG. 25 is an explanatory view showing the operation of delivering the liquid and the pipette chips in the automatic apparatus for analyzing.
Figure 26:
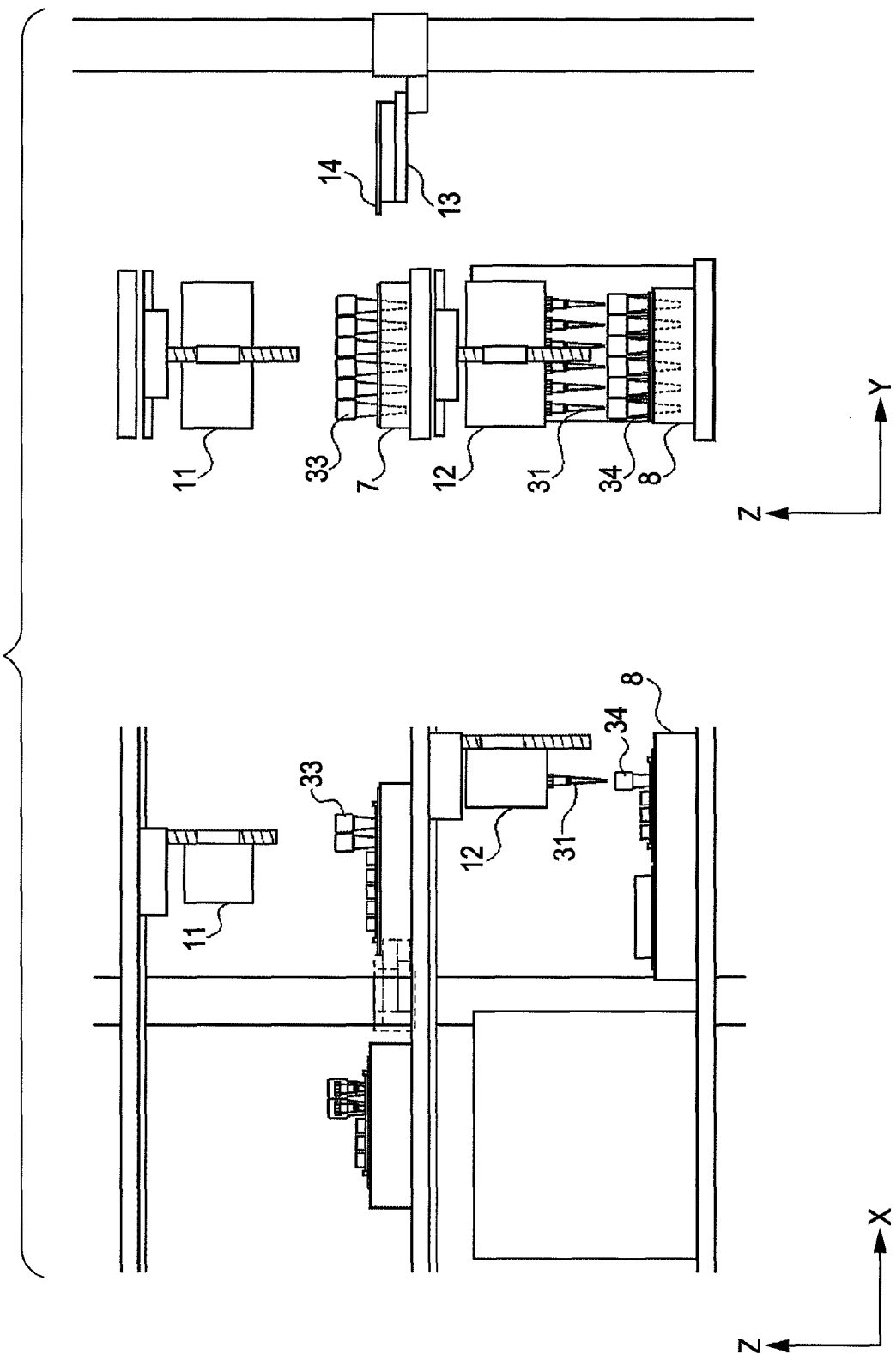
FIG. 26 is an explanatory view showing the operation of delivering the liquid and the pipette chips in the automatic apparatus for analyzing.
Figure 27:
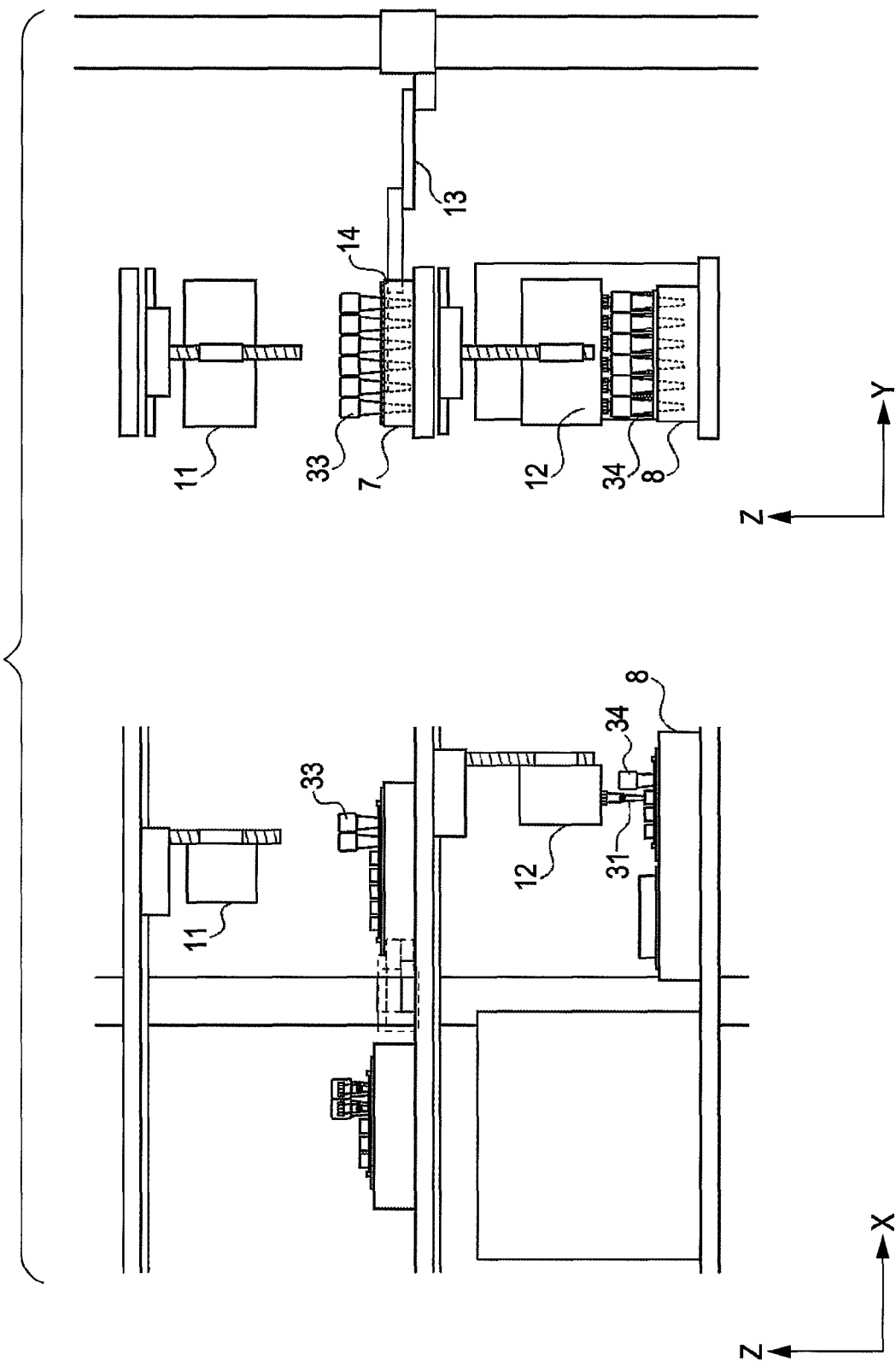
FIG. 27 is an explanatory view showing the operation of delivering the liquid and the pipette chips in the automatic apparatus for analyzing.
Figure 28:
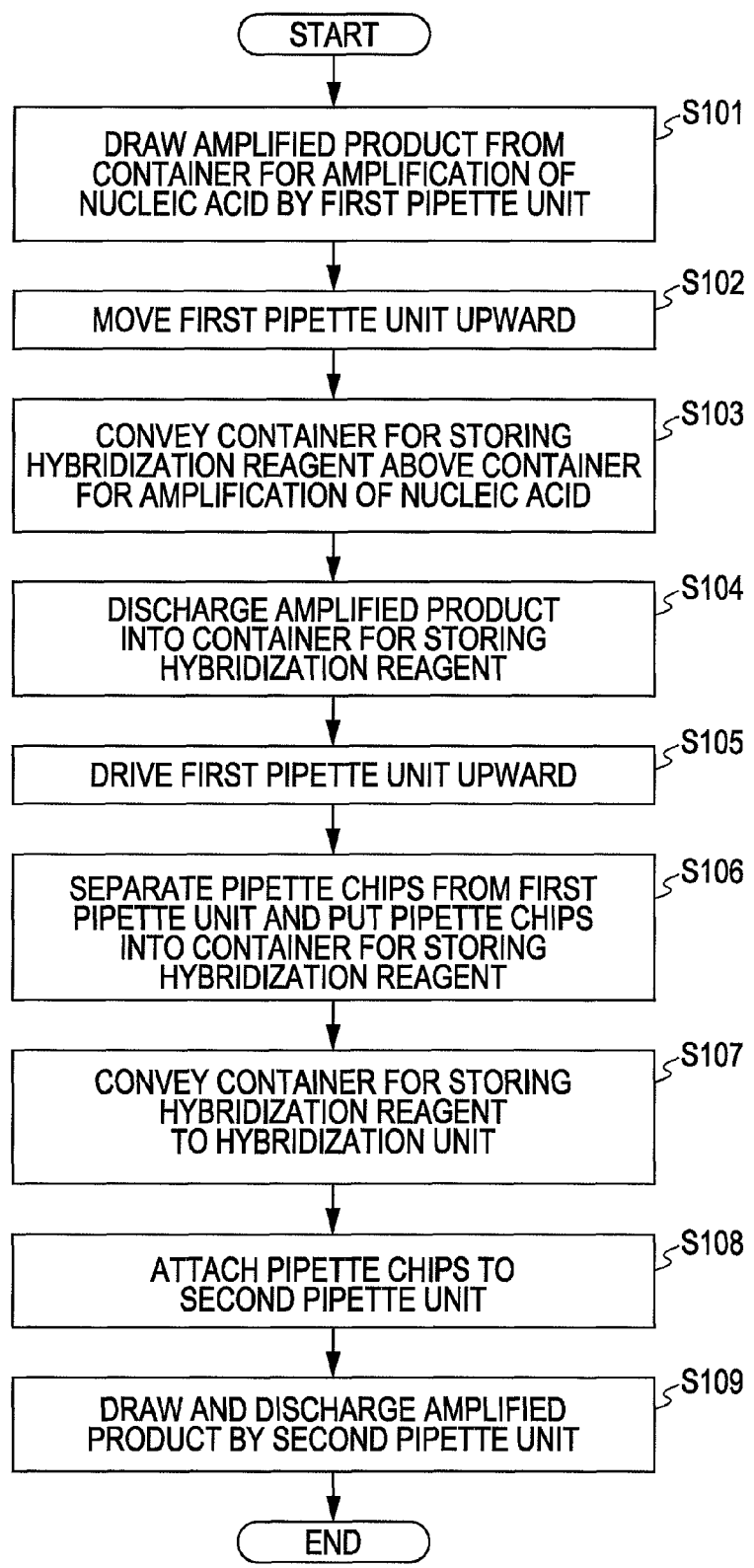
FIG. 28 is a flowchart showing the operation of delivering the liquid and the pipette chips in the automatic apparatus for analyzing.

After the completion of an amplification process, the amplified products in the container 33 for amplification of nucleic acid are drawn by the first pipette unit 11 (FIG. 12, Step S101 in FIG. 28). In a state in which the amplified products are held in the pipette chips 31, the first pipette unit 11 is lifted by the Z-axis driving mechanism (FIG. 13, Step S102 in FIG. 28). Then, the container 34 for storing hybridization reagent set in the hybridization unit 8 is held by the container hand 14 (FIG. 14). After the container 34 for storing hybridization reagent is moved aside in the +Y-direction by driving the container conveying robot 13 along the r, θ, and Z axes (FIG. 15), it is lifted to a Z-position higher than the container 33 for amplification of nucleic acid (FIG. 16), and is moved to an XY-position above the container 33 (FIG. 17, Step S103 in FIG. 28). Then, the first pipette unit 11 is lowered to a position such that the pipette chips 31 can dispense the samples to predetermined wells of the container 34 for storing hybridization reagent. In this case, the first pipette unit 11 can be driven in the X-axis direction. In this state, the samples (amplified products) are put into the predetermined wells of the container 34 for storing hybridization reagent (FIG. 18, Step S104 in FIG. 28). When the liquid has been put in the wells, the first pipette unit 11 is lifted (FIG. 19, Step S105 in FIG. 28), and is then moved to an XYZ-position where the pipette chips 31 can be put into the recesses 33a of the container 34 for storing hybridization reagent (FIG. 20). By operating a pipette-chip separation mechanism (not shown) in this state, the pipette chips 31 are transferred into the recesses 33a of the container 34 for storing hybridization reagent (FIG. 21, Step S106 in FIG. 28). Subsequently, the first pipette unit 11 is moved upward, and the container 34 for storing hybridization reagent is moved aside in the +Y-direction by the container conveying robot 13 (FIG. 22). The container 34 is lowered to a setting height such as to be set in the hybridization unit 8 (FIG. 23), and is then set therein (FIG. 24, Step S107 in FIG. 28). By then lowering the second pipette unit 12, the pipette chips 31 in the container 34 are attached to the second pipette unit 12 (FIG. 25, Step S108 in FIG. 28). After the second pipette unit 12 is temporarily lifted (FIG. 26), the samples (amplified products) in the container 34 are drawn in and discharged by the pipette chips 31 (FIG. 27, Step S109 in FIG. 28), so that the hybridization samples are arranged.

The container conveying robot 13 and the container hand 14 can be moved aside in the +Y-direction (FIG. 25) and lifted to a height such as to hold the container 33 for amplification of nucleic acid (FIG. 26), and the container 33 can be conveyed to the container recovery unit 10 while being held by the container hand 14 (FIG. 27).

The amplified products moved to the container 34 for storing hybridization reagent by the above-described operations are arranged with the reagent and used in the hybridization process. Although the pipette chips 31 moved to the container 34 for storing hybridization reagent have been used in the amplification process, they can also be used in the hybridization process for the same sample. This is because the liquid adhering on the pipette chips 31 has little influence on the hybridization process and the risk of crossover contamination of nucleic acid is low as long as the pipette chips 31 are used for the same sample.

Figure 29:
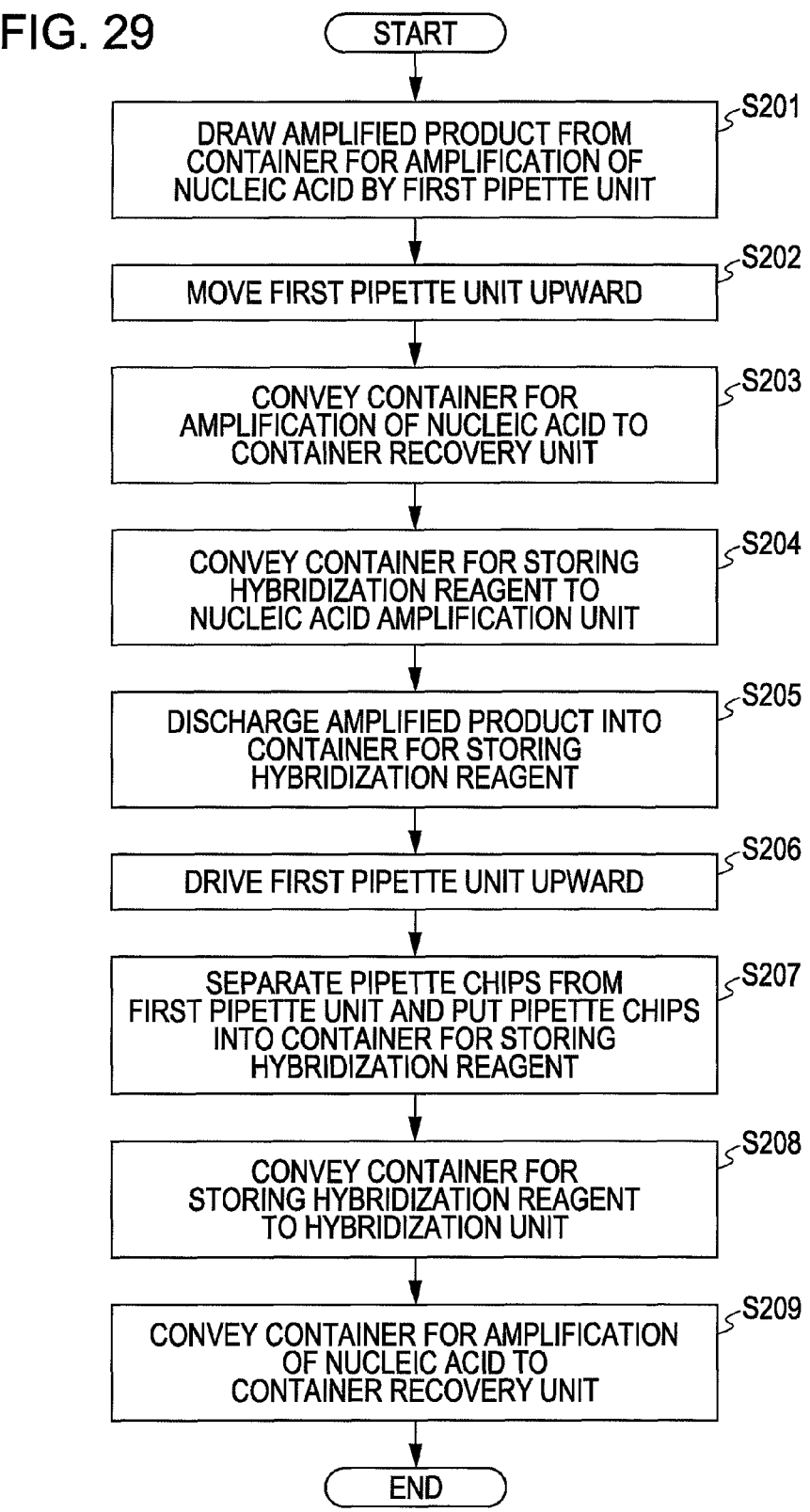
FIG. 29 is a flowchart showing a second delivery operation of delivering the liquid and the pipette chips in the automatic apparatus for analyzing.

Instead of the procedure shown in FIGS. 12 to 28, delivery of the liquid and the pipette chips, which is a characteristic of the present invention, can be performed by a procedure shown in FIG. 29.

At the start of the procedure shown in FIG. 29, the container 33 for amplification of nucleic acid is placed in the nucleic-acid amplification unit 7, and the container 34 for storing hybridization reagent is placed in the hybridization unit 8. The amplified products in the container 33 for amplification of nucleic acid are drawn by the first pipette unit 11 (Step S201), and the first pipette unit 11 is moved upward (Step S202). Subsequently, the container 33 for amplification of nucleic acid is conveyed to the container recovery unit 10 (Step S203), and the container 34 for storing hybridization reagent is then conveyed to the nucleic-acid amplification unit 7 (Step S204). This operation is a main difference from the procedure shown in FIG. 28. That is, when the amplified products and the pipette chips 31 are put in the container 34 for storing hybridization reagent, the container 34 is held by the container hand 14 in FIG. 28, and is placed in the nucleic-acid amplification unit 7 in FIG. 29.

Figure 30:
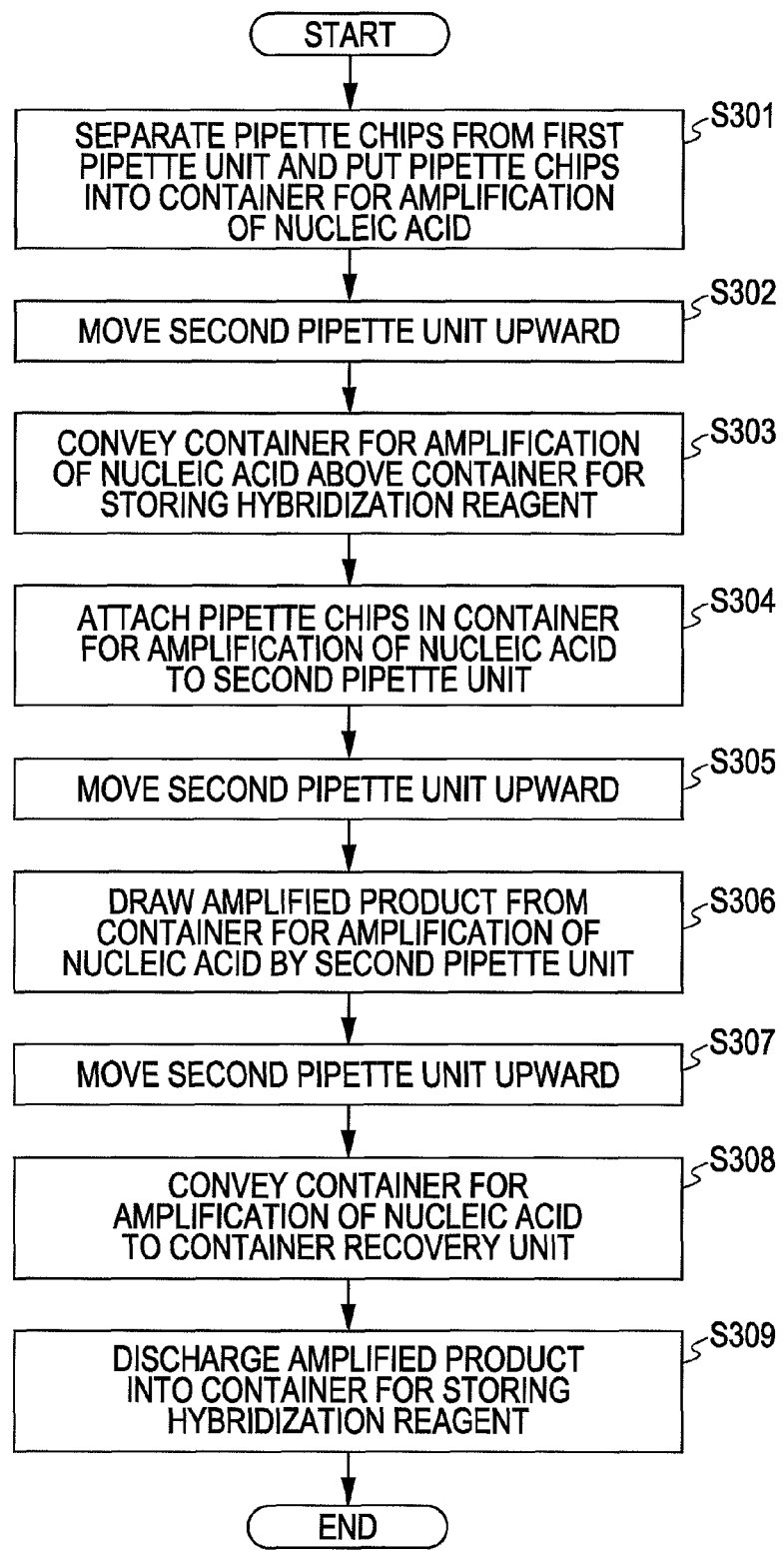
FIG. 30 is a flowchart showing a third delivery operation of delivering the liquid and the pipette chips in the automatic apparatus for analyzing.

Delivery of the liquid and the pipette chips, which is the characteristic of the present invention, can also be performed by a procedure shown in FIG. 30.

At the start of the procedure shown in FIG. 30, the container 33 for amplification of nucleic acid is placed in the nucleic-acid amplification unit 7, and the container 34 for storing hybridization reagent is placed in the hybridization unit 8. First, pipette chips 31 are separated from the first pipette unit 11, and are put into the container 33 for amplification of nucleic acid (Step S301). In this state, amplified products remain in the container 33 for amplification of nucleic acid. After the second pipette unit 12 is moved upward (Step S302), the container 33 for amplification of nucleic acid is conveyed above the container 34 for storing hybridization reagent (Step S303). With the container 33 kept in this state, the pipette chips 31 in the container 33 are attached to the second pipette unit 12 (Step S304), the second pipette unit 12 is moved up (Step S305), and the amplified products in the container 33 are drawn by the second pipette unit 12 (Step S306). Subsequently, the second pipette unit 12 is moved upward (Step S307), the container 33 is conveyed to the container recovery unit 10 (Step S308), and the amplified products are then discharged into the container 34 for storing hybridization reagent (Step S309).

As for the difference between the procedures shown in FIGS. 28 and 30, the amplified products and the pipette chips 31 are transferred from the container 33 for amplification of nucleic acid to the container 34 for storing hybridization reagent in the nucleic-acid amplification unit 7 in FIG. 28 and in the hybridization unit 8 in FIG. 30.

In the first exemplary embodiment, the first pipette unit 11 is commonly used in the nucleic-acid extraction process and the nucleic-acid amplification process, and the second pipette unit 12 is used in the hybridization process. For this reason, the nucleic-acid extraction process and the nucleic-acid amplification process can be performed independently of the hybridization process, except during the delivery operation. For example, after the nucleic-acid amplification process for the first inspection lot is completed and the samples and the pipette chips are delivered to the hybridization process, the next nucleic-acid amplification process can be started before the hybridization process is completed.

In the first exemplary embodiment, the foot print of the automatic analyzing apparatus 1 can be reduced to almost half, when compared with the case in which all three reaction units, the nucleic-acid extraction unit 6, the nucleic-acid amplification unit 7, and the hybridization unit 8, are horizontally arranged in the X-direction. In this way, it is obvious that the effect of reducing the footprint can also be obtained even when only some of the reaction units are vertically arranged. This case is covered by the scope of the present invention.

While the automatic analyzing apparatus 1 according to the first exemplary embodiment performs analysis while the reagent and the pipette chips are placed in the container shaped like a well plate, the reagent may be partly or entirely supplied by other known methods, for example, by using a disposable container only for the reagent, or by setting a reagent for a plurality of operations in a bottle. Some or all of the pipette chips may be supplied by other known methods, for example, by using a disposable container only for the pipette chips, or by setting pipette chips for a plurality of operations in a chip rack.

In the first exemplary embodiment, the samples and the pipette chips are moved by conveying the containers. Instead of using the container hand 14, a plate having recesses for holding the samples can be provided. In the operation state shown in FIG. 18, the amplified products are received by the recesses of the plate, instead of the wells of the container 34 for storing hybridization reagent. Further, in Step S306 in FIG. 30, the amplified products may be drawn from the recesses of the plate, instead of the container 33 for amplification of nucleic acid, and may be put into the container 34 for storing hybridization reagent.

Alternatively, a plate having recesses for holding the pipette chips may be provided, instead of the container hand 14. In the operation state shown in FIG. 21, the pipette chips may be received by the recesses of the plate, instead of the recesses 33*a* of the container 34 for storing hybridization reagent. In Step S304 in FIG. 30, the pipette chips may be transferred from the recesses of the plate, instead of the container 33 for amplification of nucleic acid, to the second pipette unit 12.

When the above-described plate is used, carry-over contamination may be caused by carrying over the samples to the next and subsequent analysis operations. Therefore, it is preferable to provide a mechanism for cleaning the plate.

Instead of the samples, liquid, such a reagent different from the sample, may be delivered.

Further alternatively, a solid-state sample may be delivered, instead of the liquid-state sample. In this case, it is preferable to use a sample picking mechanism different from the combination of the pipette chips and the pipette unit. For example, it is conceivable to use a pinching mechanism like tweezers, a scooping mechanism, and a mechanism for transferring by contact.

As described above, the automatic analyzing apparatus 1 according to the first exemplary embodiment can perform complicated biochemical reaction treatment without increasing the footprint thereof. Particularly, the width of the automatic analyzing apparatus 1 can be reduced to about half the width provided when all the treatment units are arranged in the horizontal direction.

Second Exemplary Embodiment

Figure 31:
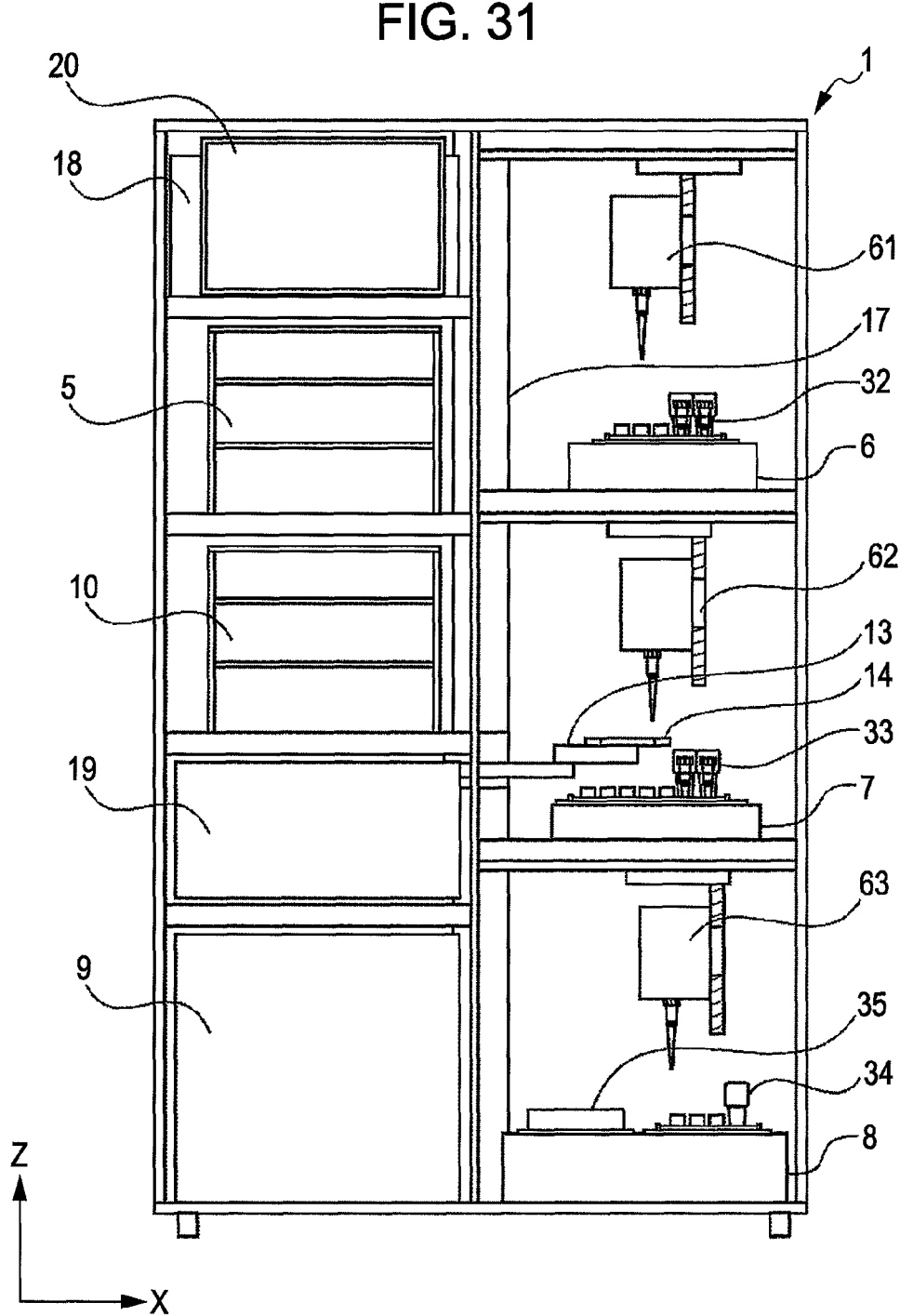
FIG. 31 is a front sectional view of an automatic apparatus for analyzing according to a second exemplary embodiment of the present invention.

FIG. 31 is a schematic front view showing an internal configuration of an automatic analyzing apparatus 1 according to a second exemplary embodiment of the present invention.

FIG. 31 shows the entire automatic analyzing apparatus 1. In the automatic analyzing apparatus 1, liquid reaction units are stacked on the right side, as viewed from the front side.

In the second exemplary embodiment, samples and pipette chips are delivered between the treatment units at the following two positions, that is, (1) from a nucleic-acid extraction unit 6 to a nucleic-acid amplification unit 7 and (2) from the nucleic-acid amplification unit 7 to a hybridization unit 8. The delivery operations can be performed similarly to the operations performed in the first exemplary embodiment shown in FIGS. 12 to 30. However, since more types of delivery operations are performed than in the first exemplary embodiment, it is necessary to devise the sequence control.

In the second exemplary embodiment, a nucleic-acid extraction process, a nucleic-acid amplification process, and a hybridization process are performed with independent pipette units. For this reason, these three processes can be easily performed in parallel.

Third Exemplary Embodiment

An automatic apparatus for analyzing according to a third exemplary embodiment analyzes a sample by an antigen-antibody reaction using a chip in which an antigen or an antibody is fixed to a substrate.

More specifically, the automatic analyzing apparatus for nucleic acid in the first or second exemplary embodiment can be diverted. An automatic analyzing apparatus that analyzes a sample by an antigen-antibody reaction can be obtained by changing the nucleic-acid amplification unit 7 to a second reaction unit that causes a reaction by adding a secondary antibody to the chip and changing the hybridization unit 8 to a cleaning unit for removing the antigen or the antibody that is not concerned with bonding.

An automatic apparatus for analyzing according to a fourth exemplary embodiment of the present invention utilizes bacterial culture.

More specifically, the automatic analyzing apparatus for nucleic acid in the first or second exemplary embodiment can be can be diverted. An automatic analyzing apparatus that analyzes a sample by bacterial culture can be obtained by changing the process performed by the nucleic-acid amplification unit 7 shown in FIG. 1 to a first cell culture process performed in a culture bottle and changing the process performed by the hybridization unit 8 to a secondary cell culture process performed in a culture medium.

The present invention is not limited to the above embodiments and various changes and modifications can be made within the spirit and scope of the present invention. Therefore to apprise the public of the scope of the present invention, the following claims are made.

This application claims the benefit of Japanese Application No. 2007-104850 filed Apr. 12, 2007, which is hereby incorporated by reference herein in its entirety.

What is claimed is:

1. An apparatus for biochemical analysis, comprising:
   at least two treatment units arranged in a vertical direction and configured to subject a sample to biochemical reaction treatment or biochemical detection treatment;
   two layers each having at least one of the treatment units;
   two pipette units each of which is arranged at a respective one of the two layers, each of the two pipette units having a moving mechanism in a first horizontal direction; and
   a conveying mechanism configured to convey the sample in the vertical direction and to deliver the sample from one of the treatment units to the other treatment unit,
   wherein each of the two pipette units is configured to hold a plurality of pipette chips so as to be arranged in a single line in a horizontal second direction orthogonal to the first horizontal direction.

2. The apparatus according to claim 1, wherein the conveying mechanism includes first and second sample conveying mechanisms configured to independently convey the sample, and the sample is delivered between the first and second sample conveying mechanisms during conveyance, and wherein the first sample conveying mechanism comprises one of the two pipette units.

3. The apparatus according to claim 2, wherein the first sample conveying mechanism is configured to deliver the sample to the second sample conveying mechanism above at least one of the treatment units.

4. The apparatus according to claim 2, wherein the second sample conveying mechanism is configured to convey a container capable of holding the sample, and the sample is delivered from the first sample conveying mechanism to the container in the treatment units.

5. The apparatus according to claim 1, wherein the conveying mechanism includes a pipette chip conveying mechanism configured to convey one of the pipette chips, and wherein the one of the pipette chips is delivered from one of the two pipette units to the pipette chip conveying mechanism above at least one of the treatment units, and the delivered pipette chip is attached to the other one of the two pipette units.

6. The apparatus according to claim 1, wherein the conveying mechanism includes a container conveying mechanism configured to convey a container capable of holding one of the pipette chips, and wherein the one of the pipette chips is delivered from one of the two pipette units to the container in the treatment units, and the delivered pipette chip is attached to the other one of the two pipette units.

7. The apparatus according to claim 1, wherein the conveying mechanism comprises a robot mechanism with a hand configured to hold a container, and wherein the hand comprises holes for vacuum adsorption.

8. A biochemical analysis method of using an apparatus including a first layer and a second layer arranged in a vertical direction, and a conveying mechanism, wherein the first layer comprises a first treatment unit and a first pipette unit having a moving mechanism in a first horizontal direction, and the second layer comprises a second treatment unit and a second pipette unit having a moving mechanism in the first horizontal direction, comprising the steps of:
  subjecting a sample to biochemical reaction treatment or biochemical detection treatment in the first treatment unit by using the first pipette unit;
  conveying the sample in the vertical direction by using the conveying mechanism;
  delivering the sample to the second treatment unit by using the conveying mechanism; and
  subjecting the sample to biochemical reaction treatment or biochemical detection treatment in the second treatment unit by using the second pipette unit,
  wherein each of the first and second pipette units is configured to hold a plurality of pipette chips so as to be arranged in a single line in a horizontal second direction orthogonal to the first horizontal direction.

9. An apparatus for biochemical analysis, comprising:
a first layer comprising: a first treatment unit configured to subject a sample to biochemical reaction treatment; and a first pipette unit having a moving mechanism in a first horizontal direction;
a second layer arranged in a vertical direction of the first layer, comprising:
a second treatment unit configured to subject the sample to biochemical detection treatment; and a second pipette unit having a moving mechanism in the first horizontal direction; and
a conveying mechanism configured to convey the sample in the vertical direction and to deliver the sample from one of the first and second layers to the other of the first and second layers,
wherein each of the first and second pipette units is configured to hold a plurality of pipette units so as to be arranged in a single line in a horizontal second direction orthogonal to the first horizontal direction.

* * * * *